US011213512B2

(12) United States Patent
Gokel et al.

(10) Patent No.: US 11,213,512 B2
(45) Date of Patent: Jan. 4, 2022

(54) BIS-AMINO ACID BASED COMPOUND AND USE THEREOF

(71) Applicant: THE CURATORS OF THE UNIVERSITY OF MISSOURI, Columbia, MO (US)

(72) Inventors: George W Gokel, St. Louis, MO (US); Joseph W Meisel, St. Louis, MO (US); Mohit B Patel, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 14 days.

(21) Appl. No.: 16/311,441

(22) PCT Filed: Jun. 20, 2017

(86) PCT No.: PCT/US2017/038355
§ 371 (c)(1),
(2) Date: Dec. 19, 2018

(87) PCT Pub. No.: WO2017/223098
PCT Pub. Date: Dec. 28, 2017

(65) Prior Publication Data
US 2019/0201379 A1    Jul. 4, 2019

Related U.S. Application Data

(60) Provisional application No. 62/352,983, filed on Jun. 21, 2016.

(51) Int. Cl.
| | |
|---|---|
| *C07K 5/06* | (2006.01) |
| *A61K 31/4045* | (2006.01) |
| *A61K 31/65* | (2006.01) |
| *A61K 31/473* | (2006.01) |
| *A61K 31/7048* | (2006.01) |
| *A61K 31/7036* | (2006.01) |
| *C07D 209/20* | (2006.01) |
| *A61K 31/405* | (2006.01) |
| *A61K 45/06* | (2006.01) |
| *A61P 31/04* | (2006.01) |
| *A61K 31/167* | (2006.01) |
| *A61K 31/43* | (2006.01) |
| *A61K 31/496* | (2006.01) |
| *A61K 31/702* | (2006.01) |

(52) U.S. Cl.
CPC ........ *A61K 31/4045* (2013.01); *A61K 31/167* (2013.01); *A61K 31/405* (2013.01); *A61K 31/473* (2013.01); *A61K 31/65* (2013.01); *A61K 31/7036* (2013.01); *A61K 31/7048* (2013.01); *A61K 45/06* (2013.01); *A61P 31/04* (2018.01); *C07D 209/20* (2013.01); *A61K 31/43* (2013.01); *A61K 31/496* (2013.01); *A61K 31/702* (2013.01)

(58) Field of Classification Search
None
See application file for complete search history.

(56) References Cited

U.S. PATENT DOCUMENTS

| 4,783,528 | A | 11/1988 | Gokel | |
|---|---|---|---|---|
| 8,389,505 | B2 | 3/2013 | Kralj et al. | |
| 2002/0035061 | A1 | 3/2002 | Krieger et al. | |
| 2003/0198617 | A1* | 10/2003 | Green | A61K 39/39 424/85.1 |
| 2008/0287346 | A1 | 11/2008 | Svendsen et al. | |
| 2009/0062221 | A1 | 3/2009 | Dow et al. | |
| 2010/0222268 | A1 | 9/2010 | Hoffmann et al. | |
| 2011/0257254 | A1 | 10/2011 | Kralj et al. | |
| 2013/0224258 | A1 | 8/2013 | Baker | |
| 2014/0309162 | A1 | 10/2014 | Park | |
| 2016/0361292 | A1 | 12/2016 | Gokel et al. | |

FOREIGN PATENT DOCUMENTS

| WO | 9420063 | A2 | 9/1994 |
|---|---|---|---|
| WO | 2011112912 | A1 | 9/2011 |
| WO | 2015/188140 | A1 | 12/2015 |
| WO | 2017/223098 | | 12/2017 |

OTHER PUBLICATIONS

Silver et al., The Journal of Clinical Investigation, Inc., vol. 93, Apr. 1994, 1473-1480. (Year: 1994).*
Mondal et al., "A synthetic ditryptophan conjugate that rescues bacteria from mercury toxicity through complexation," Tetrahedron letters 51:6111-6115 (2010) (Year: 2010).*
Mayeno et al., "Characterization of "Peak E," a Novel Amino Acid Associated with Eosinophilia-Myalgia Syndrome," Science 250 (vol. 4988):1707-1708 (1990) (Year: 1990).*
Purushotham et al., "A Comprehensive Conformational Analysis of Tryptophan, Its Ionic and Dimeric Forms," Journal of computational chemistry 35: 595-610 (2014) (Year: 2014).*
Abel et al., "Aggregate Formation from 3-Alkylindoles: Amphiphilic Models for Interfacial Helix Anchoring Groups", Chem. Commun., 2000, pp. 433-434.
Abel et al., "Formation of Stable Vesicles from N- or 3-Alkylindoles: Possible Evidence for Tryptophan as a Membrane Anchor in Proteins", J. Org. Chem. 2000, pp. 5901-5900, vol. 65.

(Continued)

*Primary Examiner* — Julie Ha
*Assistant Examiner* — Kristina M Hellman
(74) *Attorney, Agent, or Firm* — Thompson Coburn LLP; William A. Holtz

(57) ABSTRACT

Compositions comprising bis(tryptophan) derivatives are provided that act as antimicrobials. Also provided are methods for reversing antibiotic resistance in a bacterium, or recovering or enhancing antimicrobial activity of an antibiotic against a variety of microbes, by co-administration with a bis(tryptophan) derivative.

11 Claims, 9 Drawing Sheets

(56) References Cited

OTHER PUBLICATIONS

Berenbaum, "What is Synergy?", Pharmacological Reviews, 1989, pp. 93-141, vol. 1989, No. 41.
Bolivar et al., "Construction and Characterization of New Cloning Vehhicles", Gene., 1977, pp. 95-113, vol. 2.
Carasel et al., "Halide Ions Complex and Deprotonate Dipicolinamides and Isophthalamides: Assessment by Mass Spectrometry and UV-Visible Spectroscopy", J. Org. Chem., 2010, pp. 8112-8116, vol. 75.
Chan et al., "Tryptophan- and Arginine-Rich Antimicrobial Peptides: Structures and Mechanisms of Action", Biochimica et Biophysica Acta, 2006, pp. 1184-1202, vol. 1758.
Coates et al., "Optimizing Biomimetic Gelators Constructed from Amino Acid Building Blocks", J. Org. Chem., 2007, pp. 3937-3940, vol. 72.
Doyle et al., "The Structure of the Potassium Channel: Molecular basis of K+ Conduction and Selectivity", Science, 1998, pp. 69-77, vol. 280.
Fuhrhop et al., "Molecular Monolayer Rods and Tubules Made of a-(i-Lysine),v-(Amino) Bolaamphiphiles", J. Am. Chem. Soc., 1993, pp. 1600-1601, vol. 115, No. 4.
Gale et al., "Calixpyrroles", Chem. Commun., 1998, pp. 1-8.
Gokel et al., "Synthetic Amphiphilic Peptides that Self-Assemble to Membrane-Active Anion Transporters", Anion Coordination Chemistry, First Edition, 2012, pp. 465-519, Ch 8.
Hancock et al., "Peptide Antibiotics", The Lancet, 1997, 10 pages, vol. 349, No. 9049.
Hargrove et al., "Artificial Receptors for the Recognition of Phosphorylated Molecules", Chemical Reviews, 2011, pp. 6603-6782, vol. 111.
Huang et al., "C Ring May be Dispensable for b-Carboline: Design, Synthesis, and Bioactivites Evaluation of Tryptophan Analog Derivatives Based on the Biosynthesis of b-Carboline Alkaloids", Bioorganic and Medical Chemistry, 2016, 462-473, vol. 24.
International Search Report and Written Opinion for PCT/US2015/34550 dated Aug. 26, 2015.
International Search Report and Written Opinion for PCT/US2017/038355 dated Sep. 5, 2017.
Kavallieratos et al., "A Readily Available Non-Preorganized Neutral Acyclic Halide Receptor with an Unusual Nonplanar Binding Conformation", J. Am. Chem. Soc. 1997, pp. 2325-2326, vol. 119.
Kavallieratos et al., "Hydrogen Bonding in Anion Recognition: A Family of Versatile, Nonpreorganized Neutral and Acyclic Receptors", J. Org. Chem. 1999, pp. 1675-1683, vol. 64.
Ketchem et al., "High-Resolution Conformation of Gramicidin A in a Lipid Bilayer by Solid-State NMR", Science, 1993, pp. 1457-1460, vol. 261, No. 5127.
Koulov et al., "Facilitated Transport of Sodium or Potassium Choloride Across Vesicle Membranes Using a Ditopic Salt-Binding Macrobicycle", Org. Biomol. Chem., 2003, pp. 27-29, vol. 1.
Lambert et al., "Potassium Fluxes, First Indications of Membrane Damage in Micro-Organisms", Biochemical and Biophysical Research Communications, 1973, pp. 796-799, vol. 54, No. 2.
Levy, "Active Efflux Mechanisms for Antimicrobial Resistance", Antimicrobial Agents and Chemotherapy, 1992, pp. 695-703, vol. 36, No. 4.
Meisel et al., "Reversal of Tetracycline Resistance in *Escherichia coli* by Noncytotoxic bis(Tryptophan)s", Journal of American Chemical Society, Aug. 3, 2016, pp. 10571-10577, vol. 138, Issue 33.
Meisel et al., "Tryptophan in Membrane-Active Synthetic Antimicrobials", Journal of Exploratory Research in Pharmacology, Mar. 2017, pp. 7-15, vol. 2.
Mitra et al., "Antimicrobial Activity, Biocompatibility and Hydrogelation Ability of Dipeptide-Base Amphiphiles", Organic & Biomolecular Chemistry, 2009, pp. 94-102, vol. 7.
Negin et al., "The Aqueous Medium-Dimethylsulfoxide Conundrum in Biological Studies", The Royal Society of Chemistry, 2015, pp. 8088-8093, vol. 5.
Nikaido, "Prevention of Drug Access to Bacterial Targets: Permeability Barriers and Active Efflux", Science, 1994, pp. 382-388, vol. 264.
Park et al., "Oligoether-Strapped Calix[4]pyrrole: An Ion-Pair Receptor Displaying Cation-Dependent Chloride Anion Transport", Chem. Eur. J., 2012, pp. 2514-2523, vol. 18.
Sapunaric et al., "Substitutions in the Interdomain Loop of the Tn10 TetA Efflux Transporter Alter Tetracycline Resistance and Substrate Specificity", Microbiology, 2005, pp. 2315-2322, vol. 151.
Sessler etal., "Neutral Non-Metallic Systems", Anion Receptor Chemistry. Royal Society of Chemistry: Cambridge, 2006, pp. 171-226, Ch 4.
Shai et al, "Host Defense Peptides and Lipopeptides: Modes of Action and Potential Candidates for the Treatment of Bacterial and Fungal Infections", Current Protein and Peptide Science, 2006, pp. 479-486, vol. 7.
Shai, "Mode of Action of Membrane Active Antimicrobial Peptides", Pept. Sci., 2002, pp. 236-248, vol. 66.
Shin et al., "Dehydrooligopeptides. XV. Useful Syntheses of Dehydrodipeptides by the Enzymatic Coupling of a-Dehydroglutamate with Various a-Amino Acid Amides Using Proteases", Bull. Chem. Soc. Jpn., 1993, pp. 2048-2053, vol. 66, No. 7.
Straus et al., "Mode of Action of the New Antibiotic for Gram-Positive Pathogens Daptomycin: Comparison with Cationic Antimicrobial Peptides and Lipopeptides", Biochimica et Biophysica Acta, 2006, pp. 1215-1223, vol. 1758.
Sun et al., "Bacterial Multidrug Efflux Pumps: Mechanisms, Physiology and Pharmacological Exploitations", Biochemical and Biophysical Research Communications, 2014, pp. 254-267, vol. 453.
Thanassi et al., "Role of Outer Membrane Barrier in Efflux-Mediated Tetracycline Resistance of *Escherichia coli*", Journal of Bacteriology, 1995, pp. 998-1007, vol. 177, No. 4.
Vig et al., "Amino Acid Ester Prodrugs of Floxuridine: Synthesis and Effects of Structure, Stereochemistry, and Site of Esterification on the Rate of Hydrolysis", Pharmaceutical Research, 2003, pp. 1381-1388, vol. 20, No. 9.
Yamnitz et al., "Dianilides of Dipicolinic Acid Function as Synthetic Chloride Channels", The Royal Society of Chemistry, 2010, pp. 2838-2840, vol. 46.

* cited by examiner

Bis(amino acid) + Norfloxacin          Bis(amino acid) + Ethidium bromide

Panel 13                                Panel 14

BIS-AMINO ACID BASED COMPOUND AND USE THEREOF

CROSS REFERENCE TO RELATED APPLICATIONS

This is a U.S. National Phase application of PCT application PCT/US2017/038355, filed on Jun. 20, 2017, which claims priority to U.S. Provisional Application Ser. No. 62/352,983 filed Jun. 21, 2016, both of which are incorporated herein by reference in their entireties.

GOVERNMENT RIGHTS STATEMENT

This invention was made with Government support under CHE-1307324 awarded by the National Science Foundation. The Government has certain rights in the invention.

FIELD OF INVENTION

The present invention relates to the fields of antimicrobials. More specifically, the present invention relates to bis-amino acid based compounds that can be used as antimicrobials or can be used to recover or enhance the efficacy of existing antimicrobials.

BACKGROUND OF INVENTION

Antibiotic resistance has become a major health crisis. Bacteria have developed resistance to most of the known antibiotics and the rate of discovery of new antibiotics has decreased dramatically in recent years. Patients who suffer from multidrug resistant (MDR) bacteria have few treatment options available.

The current interest in anion binding molecules can hardly be overstated. Numerous reviews of the area have appeared including two monographs (Hargrove, et al., Chem. Rev. 2011, 111, 6603-6782; Bowman-James, et al., Anion Coordination Chemistry. Eds.; Wiley VCH: New York, 2012, 574 pp; Sessler, et al.; Anion Receptor Chemistry. Royal Society of Chemistry: Cambridge, 2006; 413 pp). Many of the anion binders derive from early work reported by Crabtree and coworkers (Kavallieratos, et al., J. Am. Chem. Soc. 1997, 119, 2325-2326; Kavallieratos, et al., J. Org. Chem. 1999, 64, 1675-1683) who showed that arenes having meta-dicarboxylic acids, e.g. isophthalic acid, could form bis(amide)s that readily bound such spherical ions as chloride and bromide. The tris-arene hydrogen bond stabilization system was incorporated into a cryptand-like structure along with a crown ether and the combination functioned as a salt binder (Koulov, et al., Org. Biomol. Chem. 2003, 1, 27-29). Multiple hydrogen bonds are available for anion stabilization in cycles such as those known as calixpyrroles (Gale, et al., Chem. Commun. 1998, 1-8; Park, et al., Chem. Eur. J. 2012, 18, 2514-2523).

Substituted bis(anilide)s of isophthalic and dipicolinic acid were previously reported (Carasel, et al., J. Org. Chem. 2010, 75, 8112-8116). These compounds were, like many tris-arenes, poorly soluble in water but certain of them formed channels in bilayer membranes (Yamnitz, et al., Chem. Commun. 2010, 46, 2838-2840). In addition, indole was previously disclosed possibly functioning as an amphiphilic head group (Abel, et al., Chem. Commun. 2000, 433-434; and Abel, et al., J. Org. Chem. 2000, 65, 5901-5909). Stable liposomes were formed from either 3- or N-substituted n-decyl- or n-octadecylindoles. The "head group" capability of tryptophan's indole is apparent in biology. The Leu-Trp repeats of gramicidin (Ketchem, et al., Science 1993, 261, 1457-1460) and the tryptophans present only at the membrane interfaces in the KcsA voltage gated potassium channel (Doyle, et al., Science 1998, 280, 69-77) support this inference.

Therefore, there is an urgent need for new compounds such as synthetic anion binders that act as antimicrobials and/or that recover or enhance the efficacy of existing antibiotics against MDR bacteria or "Superbugs".

SUMMARY OF INVENTION

Nine bis(tryptophan) derivatives (BTs) and two control compounds were synthesized and tested for antimicrobial activity against two *Escherichia coli* strains and a *Staphylococcus aureus* strain. The effects of linker type, shape, and conformational rigidity were manifested in dramatic differences in altering tetracycline potency when co-administered with that antibiotic. A reversal of resistance was observed for an *E. coli* strain having a TetA efflux pump. Survival of mammalian cells was assayed with good result.

Provided herein is an antimicrobial composition comprising a bis(tryptophan) derivative. In certain embodiments, the bis(tryptophan) derivative comprises an arenyl, alkyl, aralkyl, or unsaturated spacer, a charged ammonium moiety, and indole in a tryptophan residue.

Also provided herein is a method of reversing antibiotic resistance in a bacterium. This method comprises administering to the bacterium the antibiotic with a bis(tryptophan) derivative. In certain embodiments, the bis(tryptophan) derivative comprises an arenyl, alkyl, aralkyl, or unsaturated spacer, a charged ammonium moiety, and indole in a tryptophan residue.

Further provided herein is a method of recovering or enhancing antimicrobial activity of an antibiotic. This method comprises administering to a bacterium the antibiotic with a bis(tryptophan) derivative. In certain embodiments, the bis(tryptophan) derivative comprises an arenyl, alkyl, aralkyl, or unsaturated spacer, a charged ammonium moiety, and indole in a tryptophan residue.

DETAILED DESCRIPTION OF INVENTION

Figure 1:
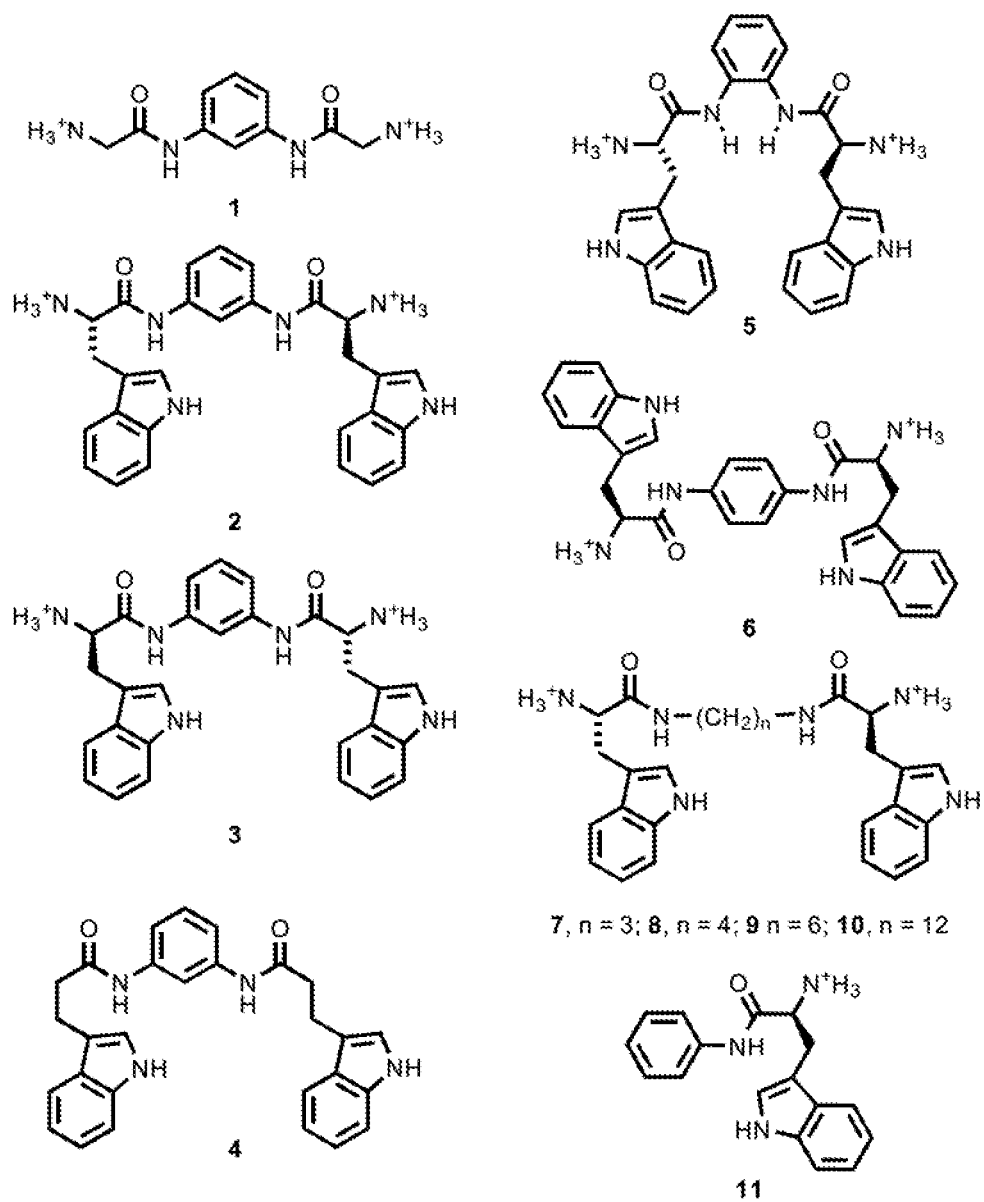
FIG. 1 illustrates chemical structures of compounds 1-11.

It is to be noted that the term "a" or "an" entity refers to one or more of that entity; for example, "an antibiotic" is understood to represent one or more antibiotics. As such, the terms "a" (or "an"), "one or more," and "at least one" can be used interchangeably herein.

Unless defined otherwise, all technical and scientific terms used herein have the same meaning as commonly understood by one of ordinary skill in the art to which this disclosure is related.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole.

A series of nine bis(tryptophan) derivatives (BTs) and two control compounds were synthesized and tested for antimicrobial activity herein. As used herein, the "antimicrobial activity" of an antimicrobial agent is defined as the property of a substance to inhibit the growth and reproduction of a microbial organism or to kill it. Common terms generally applied to bacteria are bacteriostatic (stops growth) and bactericidal (kills bacteria). Depending on the concentrations applied, microbial growth can be slowed or stopped in comparison to concurrent experiments conducted in the absence of an antimicrobial agent. Depending on the concentrations applied, additional microbe death can occur in comparison to concurrent experiments conducted in the absence of an antimicrobial agent. The results of minimum inhibitory concentration (MIC) evaluations are presented herein and the conditions are specified. The MIC is the lowest concentration of any agent having antimicrobial activity that inhibits the growth of a microorganism as judged by optical density analysis using a spectrophotometer. MIC can be determined by inoculating media with the organism and adding the antimicrobial agent diluted successively in half. After an appropriate incubation time, the MIC is evaluated by inspection as the transition between two successive 2-fold dilutions in which the one concentrated sample is clear and growth is apparent in the 2-fold less concentrated sample. Reference herein to increasing or enhancing activity, efficacy, potency, and the like are used interchangeably to mean that when the bis(tryptophan) derivative is present, the ability of the antimicrobial agent to inhibit the growth of or to kill an organism will be manifested at a concentration lower than would be required to achieve the same results in the absence of said bis(tryptophan) derivative.

Certain aspects are drawn to an antimicrobial composition comprising a bis(tryptophan) derivative. In certain embodiments, the bis(tryptophan) derivative (BT) comprises an arenyl, alkyl, aralkyl, or unsaturated spacer, a charged ammonium moiety, and indole in a tryptophan residue. The effect of arylene and alkylene linkers on the bacteriostatic activity of the compounds was assessed against two E. coli strains and a S. aureus strain. Structure-based studies revealed that in arylene-linked BTs the meta positioning of two tryptophans and the charge of the molecules are all crucial components to observe maximal antimicrobial potency. Removal of any one property leads to loss of the antimicrobial activity. Antibacterial activity of alkylene-linked BTs was observed only for the longest dodecylene spacer. The compounds were generally more active against Gram-positive S. aureus than Gram-negative E. coli. At sub-minimum inhibitory concentrations (MIC) the meta-phenylene linked BTs recovered the antibacterial activity of tetracycline against tetracycline-resistant E. coli. This apparent synergy may arise from the membrane activity of these compounds as revealed by confocal microscopy. Minimal cytotoxicity was observed for the arylene-linked BTs at MIC concentrations against three mammalian epithelial cell lines.

Although many amphiphilic peptides have been previously reported, this study exemplifies a minimalist structure-based approach. The simplicity of the structures elaborated in this report notwithstanding, BTs effectively reversed efflux pump-mediated resistance.

In certain embodiments, the two amino acid residues in the bis(tryptophan) derivative are the same amino acid residue or two different amino acid residues. In certain embodiments, either of the two amino acid residues in the bis(tryptophan) derivative is selected from the group consisting of tryptophan, arginine, lysine and proline residues.

In certain embodiments, the bis(tryptophan) derivative is selected from the group consisting of (2S,2'S)-1,1'-(1,3-phenylenebis(azanediyl))bis(3-(1H-indol-3-yl)-1-oxopropan-2-aminium) chloride (Compound 2), (2R,2'R)-1,1'-(1,3-phenylenebis(azanediyl))bis(3-(1H-indol-3-yl)-1-oxopropan-2-aminium) chloride (Compound 3), (2S,2'S)-1,1'-(1,2-phenylenebis(azanediyl))bis(3-(1H-indol-3-yl)-1-oxopropan-2-aminium) chloride (Compound 5), (2S,2'S)-1,1'-(1,4-phenylenebis(azanediyl))bis(3-(1H-indol-3-yl)-1-oxopropan-2-aminium) chloride (Compound 6), and (S)-1-((12-((R)-2-ammonio-3-(1H-indol-3-yl)propanamido)dodecyl)amino)-3-(1H-indol-3-yl)-1-oxopropan-2-aminium chloride (Compound 10) as illustrated in FIG. 1.

Certain aspects are drawn to a method of reversing antibiotic resistance in a microbe by administering to the microbe the antibiotic with a bis(tryptophan) derivative. In certain embodiments, the bis(tryptophan) derivative comprises an arenyl, alkyl, aralkyl, or unsaturated spacer, a charged ammonium moiety, and indole in a tryptophan residue.

In certain embodiments, the two amino acid residues in the bis(tryptophan) derivative are the same amino acid residue or two different amino acid residues. In certain embodiments, either of the two amino acid residues in the bis(tryptophan) derivative is selected from the group consisting of tryptophan, arginine, lysine and proline residues. Representative examples of the bis(tryptophan) derivative include, but are not limited to, (2S,2'S)-1,1'-(1,3-phenylenebis(azanediyl))bis(3-(1H-indol-3-yl)-1-oxopropan-2-aminium) chloride (Compound 2), (2R,2'R)-1,1'-(1,3-phenylenebis(azanediyl))bis(3-(1H-indol-3-yl)-1-oxopropan-2-aminium) chloride (Compound 3), (2S,2'S)-1,1'-(1,2-phenylenebis(azanediyl))bis(3-(1H-indol-3-yl)-1-oxopropan-2-aminium) chloride (Compound 5), (2S,2'S)-1,1'-(1,4-phenylenebis(azanediyl))bis(3-(1H-indol-3-yl)-1-oxopropan-2-aminium) chloride (Compound 6), and (S)-1-((12-((R)-2-ammonio-3-(1H-indol-3-yl)propanamido)dodecyl)amino)-3-(1H-indol-3-yl)-1-oxopropan-2-aminium chloride (Compound 10) as illustrated in FIG. 1.

In certain embodiments, the antibiotic can be ampicillin, kanamycin, tobramycin, erythromycin, rifampicin, and tetracycline. Other antibiotics are exemplified herein and numerous other antibiotics, too numerous to list, are contemplated. For example, the following is a brief list of some compounds that are within the scope of the disclosure: Carbapenems such as Imipenem, Meropenem, Ertapenem, Doripenem, and Biapenem; penicillins, cephalosporins (Cefoxitin), glycopeptides (vancomycin), macrolides (azithromycin, clarithromycin), quinolones (ciprofloxacin, naldixic acid), sulfamides (sulfadiazine), isoniazid, linezolid, colistin and streptomycin.

In certain embodiments, the antibiotic is administered at a concentration below its minimum inhibitory concentration.

In certain embodiments, the bis(tryptophan) derivative is administered at a concentration below its minimum inhibitory concentration.

In certain embodiments, the antibiotic and the bis(tryptophan) derivative are both administered at a concentration below their minimum inhibitory concentrations.

In certain embodiments, the bacterium is an efflux pump expressing Gram-positive or Gram-negative bacterium, and the antibiotic resistance is efflux pump-mediated resistance. In certain embodiments, enhanced membrane permeability may counter resistance.

In certain embodiments, the bacterium is an *Escherichia coli* strain or a *Staphylococcus aureus* strain.

Certain aspects are drawn to a method of recovering or enhancing antimicrobial activity of an antibiotic by administering to a microbe the antibiotic with a bis(tryptophan) derivative. In certain embodiments, the bis(tryptophan) derivative comprises an arenyl, alkyl, aralkyl, or unsaturated spacer, a charged ammonium moiety, and indole in a tryptophan residue.

In certain embodiments, the two amino acid residues in the bis(tryptophan) derivative are the same amino acid residue or two different amino acid residues. In certain embodiments, either of the two amino acid residues in the bis(tryptophan) derivative is selected from the group consisting of tryptophan, arginine, lysine and proline residues. Representative examples of the bis(tryptophan) derivative include, but are not limited to, (2S,2'S)-1,1'-(1,3-phenylenebis(azanediyl))bis(3-(1H-indol-3-yl)-1-oxopropan-2-aminium) chloride (Compound 2), (2R,2'R)-1,1'-(1,3-phenylenebis(azanediyl))bis(3-(1H-indol-3-yl)-1-oxopropan-2-aminium) chloride (Compound 3), (2S,2'S)-1,1'-(1,2-phenylenebis(azanediyl))bis(3-(1H-indol-3-yl)-1-oxopropan-2-aminium) chloride (Compound 5), (2S,2'S)-1,1'-(1,4-phenylenebis(azanediyl))bis(3-(1H-indol-3-yl)-1-oxopropan-2-aminium) chloride (Compound 6), and (S)-1-((12-((R)-2-ammonio-3-(1H-indol-3-yl)propanamido)dodecyl)amino)-3-(1H-indol-3-yl)-1-oxopropan-2-aminium chloride (Compound 10) as illustrated in FIG. 1.

In certain embodiments, the microbe is a bacterium. In a preferred embodiment, the bacterium is an efflux pump expressing Gram-positive or Gram-negative bacterium, and the antibiotic resistance is efflux pump-mediated resistance. Representative examples of the bacterium include, but are not limited to, an *Escherichia coli* strain or a *Staphylococcus aureus* strain. Bacterial stains such as *Klebsiella pneumoniae, Acinetobacter baumannii, Clostridium difficile, Mycobacterium tuberculosis*, vancomycin resistant *enterococcus*, methicillin resistant *Staphylococcus aureus* and *Pseudomonas aeruginosa* are also included.

In certain embodiments, the antibiotic can be ampicillin, kanamycin, tobramycin, erythromycin, rifampicin, and tetracycline. Other antibiotics are exemplified herein and numerous other antibiotics, too numerous to list, are contemplated. For example, the following is a brief list of some compounds that are within the scope of the disclosure: Carbapenems such as Imipenem, Meropenem, Ertapenem, Doripenem, and Biapenem; penicillins, cephalosporins (Cefoxitin), glycopeptides (vancomycin), macrolides (azithromycin, clarithromycin), quinolones (ciprofloxacin, naldixic acid), sulfamides (sulfadiazine), isoniazid, linezolid, colistin and streptomycin.

In certain embodiments, the antibiotic is administered at a concentration below its minimum inhibitory concentration.

In certain embodiments, the bis(tryptophan) derivative is administered at a concentration below its minimum inhibitory concentration.

In certain embodiments, the antibiotic and the bis(tryptophan) derivative are both administered at a concentration below their minimum inhibitory concentrations.

Certain aspects are drawn to the administration of bis(tryptophan) derivatives with antimicrobial agents. In certain embodiments, the bis(tryptophan) derivative comprises an arenyl, alkyl, aralkyl, or unsaturated spacer, a charged ammonium moiety, and indole in a tryptophan residue. A combination of the antimicrobial agent and the bis(tryptophan) derivatives can be administered by any route, protocol, means, etc., appropriate for its administration and embodiments are not limited to any particular route, protocol, means, etc. of administration. For example, the antibiotic and bis(tryptophan) derivatives can be administered to the microbe such as by contacting the microbe in culture or in solution or by applying the antibiotic and bis(tryptophan) derivatives to a material, such as the surface of a material, in or on which the microbe resides. Administration can be to a subject having a microbial infection and such administration to the subject results in administration to the microbe. For example, the subject can be a plant or an animal. In certain embodiments, the subject can be a mammal. In certain embodiments, the mammal subject can be a human having and suffering from a microbial infection. In certain embodiments, a combination of an antibiotic and a bis(tryptophan) derivative as disclosed herein is administered in an effective amount. An "effective amount" is that amount, the administration of which to a subject (also referred to as a patient), either in a single dose or as part of a series, is effective for treatment. For example, an effective amount can be an amount that is sufficient to reduce the severity of a microbial infection (or one or more symptoms thereof), ameliorate one or more symptoms of an infection, prevent the advancement of the infection, cause regression of infection, or enhance or improve the therapeutic effect(s) of another therapy. In some embodiments, the effective amount cannot be specified in advance and can be determined by a caregiver, for example, by a physician or other healthcare provider, using various means, for example, dose titration. Appropriate therapeutically effective amounts can also be determined by routine experimentation using, for example, animal models.

In certain embodiments, the antimicrobial agent and the bis(tryptophan) derivative can be administered orally, intravenously, intramuscularly, intraperitoneally, by ointment, cream or any other topical or surface application or surface coating. A medical device or material, e.g., catheters, could be coated with the bis(tryptophan) derivative. As a result, the bis(tryptophan)s could also be used for preventing the growth of bacteria on a surface or in culture. The bis(tryptophan) derivatives could also be used as a prophylactic to prevent development of bacterial infections. The antimicrobial agent and bis(tryptophan) derivative can be administered in a single treatment or administered multiple times such as on a schedule or in a series over a period of time. The antimicrobial agent and the bis(tryptophan) derivative can be administered at the same time or at practically the same time, such as immediate sequential administration. In certain embodiments, the antimicrobial agent and the bis(tryptophan) derivative are pre-combined with each other into a composition comprising a combination of antimicrobial agent and bis(tryptophan) derivative. In certain embodiments, the antimicrobial agent can be administered first followed by administration of the bis(tryptophan) derivative. In certain embodiments, the bis(tryptophan) derivative can be administered first followed by administration of the antimicrobial agent. The antimicrobial agent is considered to be administered with the bis(tryptophan) derivative so long as both compositions are simultaneously contacted with a microbe even if not simultaneously applied, such as simultaneous in a culture with a microbe, simultaneously on a surface with a microbe, or simultaneously in a subject being treated. In certain embodiments, the simultaneous presence of both the antimicrobial agent and the bis(tryptophan) derivative act together to enhance antimicrobial activity. In certain embodiments, the simultaneous presence of both the antimicrobial agent and the bis(tryptophan) derivative reverse the resistance of a microbe to the anti-microbial agent.

The following disclosed embodiments are merely representative. Thus, specific structural, functional, and procedural details disclosed in the following examples are not to be interpreted as limiting.

Example 1: Compounds and Chemical Synthesis

The compounds were prepared from diaminobenzenes or from α,ω-diaminoalkanes. The amino acid, usually tryptophan, was N-Boc protected and the free carboxyl group was coupled with the appropriate diamine by using N,N,N',N'-tetramethyl-O-(1H-benzotriazol-1-yl)uronium hexafluorophosphate (HBTU). The chemical structures of these compounds are shown in FIG. 1. Compounds 1-4 are meta-phenylenediamine (meta-Ph) derivatives. Compound 1 has glycine side arms while 2 and 3 are bis(tryptophan) derivatives. The stereochemistry of the side arms in 2 and 3 varies: 2=L,L and 3=D,D. The diamine was acylated with 3-(3-indolyl)propanoic acid (IPA, sold as 3-indolepropionic acid) to form 4. Compounds 5 and 6 are isomers of 2 but the arene is substituted ortho (5) or para (6).

Compounds 7-11 are related to 2 but rather than using a meta-phenylenediamine as the spacer or connector chain, alkyl groups link the two L-tryptophans. The alkyl groups are propylene (7, $C_3$), butylene (8, $C_4$), hexylene (9, $C_6$), and dodecylene (10, $C_{12}$). Compound 11 comprises only a part of 2 and was intended to serve as a control. Note that chloride counter ions were used with all compounds except for the uncharged compound 4.

The tert-butyl carbamate-protected (Boc-protected) amino acids were coupled to the diamine using an uronium-based coupling reagent HBTU in DMF with diisopropylethylamine. After workup and isolation of the desired Boc-protected bis(amino acid) product, deprotection was carried out using hydrochloric acid dioxane/methanol and precipitated out with methylene chloride. All $^1$H- and $^{13}$C-NMR spectra were determined at 300 and 75 MHz, respectively, in CDCl$_3$ unless otherwise specified.

The tert-butyl carbamate-protected (Boc-protected) amino acids and HBTU (2.1 equivalents) were dissolved in 10 mL anhydrous DMF with diisopropylethylamine (4.0 equivalents for the neutral diamines; 6.0 equivalents for the diaminedihydrochlorides). The reaction was stirred overnight at room temperature under an argon atmosphere. The mixture was taken up in 75 mL ethyl acetate and washed with 1 M NaHSO$_4$ (2×75 mL), 5% NaHCO$_3$ (3×50 mL), and brine. The organic layer was dried by filtration through a MgSO$_4$/celite plug and the solvent removed in vacuo. The Boc-protected bis(amino acid) was used without further purification or was crystallized/precipitated from CH$_2$Cl$_2$/hexane. The deprotection was carried out by using 10 equivalents of HCl in dioxane/methanol and the product was obtained by precipitation and trituration with cold methylene chloride.

Di-tert-butyl ((1,3-phenylenebis(azanediyl))bis(2-oxoethane-2,1-diyl))dicarbamate (1a) was prepared according to the general procedure from 1,3-phenylenediamine (0.154 mg, 1.42 mmol) and Boc-Gly-OH. The product was obtained as a white powder (0.33 g, 55% yield), mp 95° C. (dec). $^1$H-NMR: δ 1.44 (s, 18H, (CH$_3$)$_3$), 3.90 (d, 2H, αCH$_2$), 5.86 (m, 2H, Boc-NH), 7.12 (t, J=7.2 Hz, 1H, phenyl H5), 7.23 (d, J=7.2 Hz, 2H, phenyl H4, H6), 7.64 (s, 1H, phenyl H2), 8.92 (s, 2H, PhNHCO—). $^{13}$C-NMR (75 MHz, CDCl$_3$): δ 28.27, 44.90, 80.28, 111.72, 116.02, 129.27, 138.00, 156.60, 168.52. HRMS (FAB$^+$): calcd for (C$_{20}$H$_{30}$N$_4$O$_6$) 422.2165, found 422.2163.

2,2'-(1,3-Phenylenebis(azanediyl))bis(2-oxoethanaminium) chloride (1) was prepared according to the general procedure using 1a (309 mg, 0.73 mmol). The product was obtained as a white powder (0.20 g, 94% yield), mp 310° C. (dec.). $^1$H-NMR (D$_2$O): δ 3.88 (s, 4H, αCH$_2$), 7.14 (d, J=8.1 Hz, 2H, phenyl H4, H6), 7.32 (t, J=8.1 Hz, 1H, phenyl H5), 7.68 (s, 1H, phenyl H2). $^{13}$C-NMR (D$_2$O): δ 40.92, 113.72, 117.97, 129.92, 136.99, 165.49. HRMS (FAB$^+$): calcd for (C$_{10}$H$_{14}$N$_4$O$_2$Na) 245.1015, found 245.1014.

Di-tert-butyl ((2S,2'S)-(1,3-phenylenebis(azanediyl))bis(3-(1H-indol-3-yl)-1-oxopropane-2,1-diyl))dicarbamate (2a) was prepared according to the general procedure using 1,3-phenylenediamine (150 mg, 1.39 mmol) and Boc-L-Trp-OH. The product was obtained as a white powder (0.80 g, 85% yield), mp 148° C. (dec). $^1$H-NMR (DMSO-d$_6$): δ1.34 (s, 18H, 2(CH$_3$)$_3$) 2.95-3.14 (ABX, 4H, 2CH$_2$β), 4.39 (ABX, 2H, 2CHα), 6.90-7.12 (m, 6H, indole H5, indole H6, ArNH), 7.15-7.40 (m, 7H, indole H2, phenylene H4), phenylene H5, indole H7), 7.68 (d, J=7.7 Hz, 2H, indole H4), 7.99 (s, 1H, phenylene H2). $^{13}$C-NMR (DMSO-d$_6$): δ 28.07, 30.59, 55.67, 77.94, 109.85, 111.15, 114.34, 118.07, 118.54, 120.76, 123.71, 127.15, 131.24, 135.89, 139.16, 155.19, 171.11. HRMS (FAB$^+$): calcd for (C$_{38}$H$_{44}$N$_6$O$_6$Na) 703.3220, found 703.3224.

(2S,2'S)-1,1'-(1,3-Phenylenebis(azanediyl))bis(3-(1H-indol-3-yl)-1-oxopropan-2-aminium) chloride (2) was prepared according to the general procedure using 2a (313 mg, 0.46 mmol). The product was obtained as a white powder (0.24 g, 94% yield), mp 223° C. (dec). $^1$H-NMR (CD$_3$OD): δ 3.33-3.53 (ABX, 4H, 2CH$_2$β), 4.26 (ABX, 2H, 2CHα), 7.01 (t, J=7.4 Hz, 2H, indole H5), 7.12 (t, J=7.0 Hz, 2H, indole H6), 7.22 (s, 2H, indole H2), 7.26 (m, 2H, phenylene H4), 7.27 (m, 1H, phenylene H5), 7.38 (d, J=8.1 Hz, 2H, indole H7), 7.67 (d, J=7.9 Hz, 2H, indole H4), 7.93 (s, 2H, phenylene H2). $^{13}$C-NMR (CD$_3$OD): δ29.01, 55.68, 107.84, 112.61, 113.28, 117.54, 119.29, 120.35, 122.93, 125.73, 128.35, 130.32, 138.32, 139.60, 168.52. HRMS (FAB$^+$): calcd for (C$_{28}$H$_{29}$N$_6$O$_2{}^+$) 481.2347, found 481.2356.

Di-tert-butyl ((2R,2'R)-(1,3-phenylenebis(azanediyl))bis(3-(1H-indol-3-yl)-1-oxopropane-2,1-diyl))dicarbamate (3a) was prepared according to the general procedure using 1,3-phenylenediamine (200 mg, 1.85 mmol) and Boc-D-Trp-OH. The product was obtained as a white powder (1.05 g, 84% yield), mp 141° C. (dec). $^1$H-NMR: δ 1.38 (s, 18H, 2(CH$_3$)$_3$) 3.10-3.45 (ABX, 4H, 2CH$_2$β), 4.62 (ABX, 2H, 2CHα), 6.90-7.23 (m, 6H, indole H5, indole H6, ArNH), 7.29-7.40 (m, 7H, indole H2, phenylene H4, phenylene H5, indole H7), 7.66 (d, J=7.0 Hz, 2H, indole H4), 8.21 (s, 1H, phenylene H2). $^{13}$C-NMR: δ 28.35, 28.98, 56.04, 80.49, 109.66, 111.63, 112.74, 116.83, 118.67, 119.35, 121.90, 123.79, 127.64, 129.34, 136.64, 138.14, 156.25, 171.58. HRMS (FAB$^+$): calcd for ($C_{38}H_{44}N_6O_6Na$) 703.3220, found 703.3219.

(2R,2'R)-1,1'-(1,3-Phenylenebis(azanediyl))bis(3-(1H-indol-3-yl)-1-oxopropan-2-aminium) chloride (3) was prepared according to the general procedure using 3a (440 mg, 0.65 mmol). The product was obtained as an off-white powder (0.23 g, 64% yield), mp 242° C. (dec). $^1$H-NMR (CD$_3$OD): δ 3.33-3.53 (ABX, 4H, 2CH$_2$β), 3.65 (s, 6H, 2NH$_3$), 4.26 (ABX, 2H, 2CHα), 7.01 (t, J=7.4 Hz, 2H, indole H5), 7.12 (t, J=7.0 Hz, 2H, indole H6), 7.22 (s, 2H, indole H2), 7.26 (m, 2H, phenylene H4), 7.27 (m, 1H, phenylene H5), 7.38 (d, J=8.1 Hz, 2H, indole H7), 7.67 (d, J=7.9 Hz, 2H, indole H4), 7.93 (s, 2H, phenylene H2). $^{13}$C-NMR (CD$_3$OD): δ 28.96, 55.67, 107.84, 112.58, 113.31, 117.55, 119.33, 120.32, 122.89, 125.76, 128.37, 130.28, 138.27, 139.56, 168.52. HRMS (FAB$^+$): calcd for ($C_{28}H_{29}N_6O_2^+$) 481.2347, found 481.2350.

N,N'-(1,3-Phenylene)bis(3-(1H-indol-3-yl)propanamide) (4) was prepared according to the general procedure using 1,3-phenylenediamine (70 mg, 0.65 mmol) and indole-3-propionic acid. The product was obtained as a white powder (0.23 g, 78% yield), mp 154-156° C. $^1$H-NMR (CD$_3$OD): δ 2.76 (t, J=7.6 Hz, 4H, 2COC$\underline{H}_2$CH$_2$-indole), 3.18 (t, 7.6 Hz, 4H, 2COCH$_2$C$\underline{H}_2$-indole), 7.04-7.39 (m, 9H, indole H5, indole H6, indole H2, phenylene H4, phenylene H6), 7.37 (d, J=7.9 Hz, 2H, indole H7), 7.60-7.66 (m, 3H, indole H4, phenylene H5). $^{13}$C-NMR (CD$_3$OD): δ 21.81, 38.37, 111.71, 114.33, 116.43, 117.53, 118.72, 119.06, 121.83, 122.40, 127.52, 137.04, 139.11, 173.38. HRMS (FAB$^+$): calcd for ($C_{28}H_{26}N_4O_2Na$) 473.1954, found 473.1945.

Di-tert-butyl ((2S,2'S)-(1,2-phenylenebis(azanediyl))bis (3-(1H-indol-3-yl)-1-oxopropane-2,1-diyl))dicarbamate (5a) was prepared according to the general procedure using 1,2-phenylenediamine (150 mg, 1.39 mmol) and Boc-L-Trp-OH. The product was obtained as a white powder (0.76 g, 80% yield), mp 129° C. (dec). Two hydrogen bonded conformations were observed spectroscopically, peaks for the major conformer are reported herein. $^1$H-NMR: δ 1.50 (s, 9H, (CH$_3$)$_3$), 3.05-3.33 (ABX, 2H, βCH$_2$), 4.21 (ABX, 1H, αCH), 5.40 (d, J=7.3 Hz, 1H, Boc-NH), 6.55-7.62 (m, 7H, ArH, ArNH), 8.98 (s, 1H, indole NH). $^{13}$C-NMR: δ 28.48, 28.84, 56.01, 80.53, 110.14, 111.55, 118.99, 119.65, 122.19, 123.45, 124.68, 126.10, 127.37, 129.33, 136.16, 155.71, 171.35. HRMS (FAB$^+$): calcd for ($C_{38}H_{44}N_6O_6Na$) 703.3220, found 703.3218.

(2S,2'S)-1,1'-(1,2-Phenylenebis(azanediyl))bis(3-(1H-indol-3-yl)-1-oxopropan-2-aminium) chloride (5) was prepared according to the general procedure using 5a (600 mg, 0.88 mmol). The product was obtained as a white powder (0.21 g, 43% yield), mp 201° C. (dec). Two hydrogen bonded conformations were observed spectroscopically, peaks for the major conformer are reported herein. $^1$H-NMR (CD$_3$OD): δ 3.35-3.65 (ABX, 2H, βCH$_2$), 4.58 (t, J=6.9 Hz, 1H, αCH), 7.00-7.73 (m, 7H, ArH, ArNH). $^{13}$C-NMR (CD$_3$OD): δ 28.79, 55.74, 107.93, 112.56, 119.58, 120.36, 122.92, 125.81, 126.35, 127.36, 128.48, 130.99, 138.27, 169.44. HRMS (FAB$^+$): calcd for ($C_{28}H_{29}N_6O_2^+$) 481.2347, found 481.2359.

Di-tert-butyl ((2S,2'S)-(1,4-phenylenebis(azanediyl))bis (3-(1H-indol-3-yl)-1-oxopropane-2,1-diyl))dicarbamate (6a) was prepared according to the general procedure using 1,4-phenylenediamine (150 mg, 1.39 mmol) and Boc-L-Trp-OH. The product was obtained as a white powder (0.84 g, 89% yield), mp 167° C. (dec). $^1$H-NMR (CD$_3$OD): δ 1.41 (s, 9H, (CH$_3$)$_3$), 3.19-3.36 (ABX, 2H, βCH$_2$), 4.47 (ABX, 1H, αCH), 6.98-7.12 (m, 3H, indole H5, indole H6, indole H2), 7.27-7.42 (m, 3H, indole H7, phenylene CH), 7.61 (d, J=7.7 Hz, 1H, indole H4), 7.78 (s, 1H, indole NH). $^{13}$C-NMR (CD$_3$OD): δ 28.50, 29.26, 56.66, 80.52, 110.06, 111.90, 118.97, 119.50, 121.52, 122.07, 124.15, 128.14, 134.88, 137.26, 156.85, 172.14. HRMS (FAB$^+$): calcd for ($C_{38}H_{44}N_6O_6Na$) 703.3220, found 703.3210.

(2S,2'S)-1,1'-(1,4-Phenylenebis(azanediyl))bis(3-(1H-indol-3-yl)-1-oxopropan-2-aminium) chloride (6) was prepared according to the general procedure using 6a (475 mg, 0.70 mmol). The product was obtained as a white powder (0.36 g, 93% yield), mp 237° C. (dec.). $^1$H-NMR (CD$_3$OD): δ 3.34-3.54 (ABX, 2H, βCH$_2$), 4.27 (ABX, 1H, αCH), 6.97-7.14 (m, 2H, indole H5, indole H6), 7.24 (s, 1H, indole H7), 7.38 (d, J=8.1 Hz, 1H, indole H7), 7.67 (d, J=7.9 Hz, 1H, indole H4). $^{13}$C-NMR (75 MHz, CDCl$_3$): δ 28.93, 55.69, 107.90, 112.57, 119.33, 120.29, 121.88, 122.87, 125.72, 128.38, 135.61, 138.26, 168.33. HRMS (FAB$^+$): calcd for ($C_{28}H_{28}N_6O_2Na$) 503.2171, found 503.2166.

Di-tert-butyl ((2S,2'S)-(propane-1,3-diylbis(azanediyl)) bis(3-(1H-indol-3-yl)-1-oxopropane-2,1-diyl))dicarbamate (7a) was prepared according to the general procedure using 1,3-diaminopropane dihydrochloride (200 mg, 1.36 mmol) and Boc-L-Trp-OH. The product was obtained as a white powder (0.51 g, 58% yield). The compound was previously reported (Kumar, et al., *Oncol. Res.* 2003, 14, 247-265) and the spectra obtained matched those previously reported.

(2S,2'S)-1,1'-(Propane-1,3-diylbis(azanediyl))bis(3-(1H-indol-3-yl)-1-oxopropan-2-aminium) chloride (7) was prepared according to the general procedure using 7a (380 mg, 0.59 mmol). The product was obtained as a white powder (0.30 g, 98% yield), mp 234° C. (dec). $^1$H-NMR (CD$_3$OD): δ 1.40 (m, 2H, —C$\underline{H}_2$CH$_2$NH—), 2.98 (m, 4H, —CH$_2$C$\underline{H}_2$NH—), 3.22-3.65 (m, 4H, CH$_2$β), 4.13 (ABX, 2H, CHα), 6.99-7.18 (m, 4H, indole H5, indole H6), 7.25 (s, 2H, indole H2), 7.39 (d, J=6.4 Hz, 2H, indole H7), 7.69 (d, J=4.7 Hz, 2H, indole H4), 8.30 (br, CONH). $^{13}$C-NMR (CD$_3$OD): δ 28.78, 29.39, 37.76, 55.27, 108.03, 112.62, 119.34, 120.22, 122.80, 125.71, 128.29, 138.02, 170.05. HRMS (FAB$^+$): calcd for ($C_{25}H_{31}N_6O_2^+$) 447.2503, found 447.2503.

Di-tert-butyl ((2S,2'S)-(butane-1,4-diylbis(azanediyl))bis (3-(1H-indol-3-yl)-1-oxopropane-2,1-diyl))dicarbamate (8a) was prepared according to the general procedure using 1,4-diaminobutane dihydrochloride (210 mg, 1.30 mmol) and Boc-L-Trp-OH. The product was obtained as a white powder (0.79 g, 92% yield). The compound was previously reported (Kumar, et al., *Oncol. Res.* 2003, 14, 247-265) and the spectra obtained matched those previously reported.

(S)-1-((4-((R)-2-Ammonio-3-(1H-indol-3-yl)propanamido)butyl)amino)-3-(1H-indol-3-yl)-1-oxopropan-2-aminium chloride (8) was prepared according to the general procedure using 8a (650 mg, 0.98 mmol). The product was obtained as a white powder (0.51 g, 97% yield), mp 204° C. (dec). $^1$H-NMR (CD$_3$OD): δ 1.18 (m, 2H, —C$\underline{H}_2$CH$_2$NH—), 3.05 (m, 2H, —CH$_2$C$\underline{H}_2$NH—), 3.22-3.41 (ABX, 2H, CH$_2$β), 4.09 (ABX, 1H, CHα), 7.05-7.17 (m, 2H, indole H5, indole H6), 7.23 (s, 2H, indole H2), 7.40 (d, J=7.9 Hz, 1H, indole H7), 7.66 (d, J=7.9 Hz, 2H, indole H4), 8.25 (br, 1H, CONH). $^{13}$C-NMR (CD$_3$OD): δ 27.24, 29.06, 40.28, 55.40, 68.27, 108.29, 112.73, 119.38, 120.37, 123.00, 125.68, 128.51, 138.34, 170.13. HRMS (FAB$^+$): calcd for ($C_{26}H_{33}N_6O_2^+$) 461.2660, found 461.2668.

Di-tert-butyl ((2S,2'S)-(hexane-1,6-diylbis(azanediyl))bis (3-(1H-indol-3-yl)-1-oxopropane-2,1-diyl))dicarbamate (9a) was prepared according to the general procedure using 1,6-diaminohexane dihydrochloride (250 mg, 1.32 mmol) and Boc-L-Trp-OH. The product was obtained as a white powder (0.90 g, 99% yield). The compound was previously reported (Kumar, et al., *Oncol. Res.* 2003, 14, 247-265) and the spectra obtained matched those previously reported.

(2S,2'S)-1,1'-(Hexane-1,6-diylbis(azanediyl))bis(3-(1H-indol-3-yl)-1-oxopropan-2-aminium) chloride (9) was prepared according to the general procedure using 9a (650 mg, 0.94 mmol). The product was obtained as a white powder (0.33 g, 62% yield), mp 193° C. (dec). $^1$H-NMR (CD$_3$OD): δ 1.05 (m, 2H, aliphatic CH$_2$), 1.26 (m, 2H, aliphatic CH$_2$) 2.97-3.39 (m, 4H, —CH$_2$CH$_2$NH—, CH$_2$β), 4.06 (ABX, 2H, CHα), 7.02-7.15 (m, 2H, indole H5, indole H6), 7.20 (s, 1H, indole H2), 7.37 (d, J=8.1 Hz, 1H, indole H7), 7.63 (d, J=7.5 Hz, 2H, indole H4), 8.19 (br, CONH). $^{13}$C-NMR (CD$_3$OD): δ 27.38, 28.98, 29.85, 40.61, 55.29, 108.19, 112.64, 119.22, 120.27, 122.91, 125.52, 128.40, 138.26, 169.95. HRMS (FAB$^+$): calcd for (C$_{28}$H$_{37}$N$_6$O$_2^+$) 489.2973, found 489.2972.

Di-tert-butyl ((2R,2'S)-(dodecane-1,12-diylbis (azanediyl))bis(3-(1H-indol-3-yl)-1-oxopropane-2,1-diyl)) dicarbamate (10a) was prepared according to the general procedure using 1,12-diaminododecane (250 mg, 1.25 mmol) and Boc-L-Trp-OH. The product was obtained as an off-white powder (0.93 g, 96% yield), mp 86° C. (dec). $^1$H-NMR: δ 1.08-1.34 (m, 22H, aliphatic CH$_2$), 1.41 (s, 18H, C(CH$_3$)$_3$), 2.99-3.32 (m, 8H, —CH$_2$CH$_2$NH—, CH$_2$β), 4.42 (ABX, 2H, CHα), 5.36 (br, 2H, Boc-NH), 6.03 (br, 2H, CONH), 6.95 (s, 2H, indole H2) 7.03-7.16 (m, 4H, indole H5, indole H6), 7.32 (d, J=7.9 Hz, 2H, indole H7), 7.60 (d, J=7.7 Hz, 2H, indole H4). $^{13}$C-NMR: δ 26.52, 28.16, 28.54, 28.99, 29.22, 29.28, 31.43, 39.38, 55.22, 65.72, 79.83, 110.12, 111.23, 118.60, 119.27, 121.81, 123.22, 127.26, 136.19, 155.44, 171.68. HRMS (FAB$^+$): calcd for (C$_{44}$H$_{64}$N$_6$O$_6$Na) 785.4785, found 785.4792.

(S)-1-((12-((R)-2-Ammonio-3-(1H-indol-3-yl)propanamido)dodecyl)amino)-3-(1H-indol-3-yl)-1-oxopropan-2-aminium chloride (10) was prepared according to the general procedure using 10a (715 mg, 0.92 mmol). The product was obtained as a white powder (0.56 g, 93% yield), mp 158° C. (dec). $^1$H-NMR (CD$_3$OD): δ 1.08-1.34 (m, 22H, aliphatic CH$_2$), 2.99-3.38 (m, 8H, —CH$_2$CH$_2$NH—, CH$_2$β), 4.04 (ABX, 2H, CHα), 7.02-7.15 (m, 4H, indole H5, indole H6), 7.20 (s, 2H, indole H2), 7.37 (d, J=7.9 Hz, 2H, indole H7), 7.62 (d, J=7.9 Hz, 2H, indole H4). $^{13}$C-NMR (CD$_3$OD): δ 27.92, 28.98, 30.01, 30.43, 30.69, 30.77, 40.77, 55.29, 108.18, 112.62, 119.20, 120.24, 122.88, 125.51, 128.40, 138.25, 169.90. HRMS (FAB$^+$): calcd for (C$_{34}$H$_{49}$N$_6$O$_2^+$) 573.3912, found 573.3929.

(S)-tert-Butyl (3-(1H-indol-3-yl)-1-oxo-1-(phenylamino) propan-2-yl)carbamate (11a) was prepared according to the general procedure using aniline (200 mg, 2.15 mmol) and Boc-L-Trp-OH. The product was obtained as a white powder (0.65 g, 80% yield). The compound was previously reported (Huang, et al., *Bioorg. Med. Chem.* 2016, 24, 462-473) and the spectra obtained matched those previously reported.

(S)-3-(1H-Indol-3-yl)-1-oxo-1-(phenylamino)propan-2-aminium chloride (11) was prepared according to the general procedure using 11a (350 mg, 0.92 mmol). The product was obtained as a white powder (0.17 g, 57% yield). The compound was previously reported (Shin, et al., *Bull. Chem. Soc. Jpn.* 1993, 66, 2048-2053) and the spectra obtained matched those previously reported.

Example 2: Bacterial Strains and Antibiotics

Two different strains of *E. coli* (Gram-negative) were used. The laboratory strain of *E. coli*, K-12 (ATCC Accession No. 700926), was used for preliminary MIC determinations. The tetracycline resistant strain of *E. coli* (Tet$^R$) was prepared by transforming competent JM109 *E. coli* (Promega) with the pBR322 plasmid (Carolina Biologicals) using the manufacturers protocol. This plasmid contains two resistance genes: the tetA gene expresses the tetracycline resistance TetA efflux pump (Sapunaric and Levy, *Microbiol.* 2005, 151, 2315-2322) and the amp$^R$ gene expresses a β-lactamase enzyme (Bolivar, et al; Gene 1977, 2, 95-113) that cleaves the four membered ring of penicillin derivatives. The resulting *E. coli*, which we designate Tet$^R$ *E. coli*, is both tetracycline and ampicillin resistant. The TetA efflux pump belongs to the major facilitator superfamily (MFS), spans the cytoplasmic membrane, and transports tetracycline from the cell cytoplasm to the periplasmic space (Thanassi, et al., *J. Bacteriol.* 1995, 177, 998-1007). This active efflux utilizes the proton gradient as an energy source (Levy, *Antimicrob. Agents Chemother.* 1992, 36, 695-703). One Gram-positive strain, *S. aureus* (ATCC Accession No. 29213), used for MIC study expresses the MFS type NorA efflux pump and is methicillin sensitive. MFS type efflux pumps are clinically relevant for resistance in both Gram-positive and Gram-negative bacteria (Sun, et al., *Biochem. Biophys. Res. Commun.* 2014, 453, 254-267). A *Staphylococcus aureus* 1199B strain that overexpresses the NorA efflux pump was also used to conduct checkerboard experiments (see, Example 8 below). This strain of *S. aureus* 1199B is resistant to both norfloxacin and ethidium bromide.

K-12 *E. coli* and *S. aureus* were acquired from ATCC. The *S. aureus* strain was used in the BSL-2 facility. K-12 *E. coli* was grown in L. B. Miller media (Sigma-Aldrich) and *S. aureus* was grown in cation adjusted MHII media (Sigma-Aldrich). Tet$^R$ *E. coli* was grown in L. B. Miller media containing 100 µg/mL Ampicillin.

The aforedescribed strains were used to determine the MIC values for BTs and to assess their ability to recover antimicrobial potency against resistant bacterial strains.

Ampicillin, tetracycline, norfloxacin and ethidium bromide were obtained from Sigma-Aldrich and dissolved in autoclaved milli-Q water before use.

Example 3: MICs and Synergy

MIC experiments were performed as described in the Clinical and Laboratory Standards Institute (CLSI) standard microdilution protocols. Bacteria was grown overnight from one CFU in media without antibiotics. Tet$^R$ *E. coli* was grown in media containing 100 µg/mL Ampicillin. On the day of experiment, bacteria were knocked back to O.D. 600 nm=0.550 in the same media. These exponential phase bacteria were then diluted in antibiotics-free media to get 4×10$^8$ CFU/mL. In a 96-well plate either L. B. Miller or MHII media was added followed by serially diluted compounds 1-11, tetracycline, or ampicillin. All the tryptophan based compounds were dissolved in DMSO and the final concentration of DMSO in each well was kept constant at 0.5% (v/v).

For the combination experiments, first, the BT or control was added to the media in the well followed by the antibiotics. The contents of the well were mixed before adding 20 µL of bacteria to get 4×10$^5$ CFU/mL per well. The plates were incubated at 37° C., 200 RPM for 24 hours before collecting results on the Biotek Cytation 3 plate reader. No more than three plates were stacked on top of each other at a time. Optical density of the wells was determined at λ=600 nm. Cells alone were considered as 0% inhibition and media alone was considered as 100% inhibition. Any inhibition greater than 80% was considered as the MIC. The results were reproduced three times before reporting.

All minimum inhibitory concentration (MIC) values for compounds 1-11 were determined according to the methods prescribed by the National Committee for Clinical Laboratory Standards (NCCLS, Methods for Dilution Antimicrobial Susceptibility Tests for Bacteria that grow aerobically; *National Committee for Clinical Laboratory Standards* 2000, 5th Edition, M7-A5). Essentially, the bacterium under study was grown to a specified optical density and added to antibiotic that was serially diluted by halves until the growth was inhibited by greater than 80%, detected spectroscopically. It is noted that MIC concentrations are sometimes reported in µg/mL. For compound 10, 10 µM corresponds to 6 µg/mL. The unit µM was used here for convenience in comparisons. The MICs that are recorded in Table 1 represent at least two replicates of three trials each. A value of >128 µM recorded in the Table means that no growth inhibition was apparent at 128 µM so the MIC could be higher.

TABLE 1

Minimal Inhibitory Concentrations (MICs)[a]

| Compound | Link (AA)[b] | E. coli K12 (µM) | E. coli Tet[R] (µM) | S. aureus (µM) |
|---|---|---|---|---|
| 1 | meta-Ph (Gly) | >128 | >128 | >128 |
| 2 | meta-Ph (L-Trp) | 64 | 48 ± 8 | 32 |
| 3 | meta-Ph (D-Trp) | 64 | 28 ± 4 | 32 |
| 4 | meta-Ph (IPA)[c] | >128 | >128 | >128 |
| 5 | ortho-Ph (L-Trp) | 64 | 56 ± 8 | 32 |
| 6 | para-Ph (L-Trp) | 128 | 120 ± 14 | 128 |
| 7 | $(CH_2)_3$ (L-Trp) | >128 | >128 | >128 |
| 8 | $(CH_2)_4$ (L-Trp) | >128 | >128 | >128 |
| 9 | $(CH_2)_6$ (L-Trp) | >128 | 128 | >128 |
| 10 | $(CH_2)_{12}$ (L-Trp) | 8 | 10 ± 2 | 4 |
| 11 | $C_6H_5$-L-Trp-$NH_2$ | >128 | >128 | >128 |

[a]MIC resolution is in powers of 2 unless otherwise indicated by a range with ±.
[b]Structure of both amino acids
[c]3-(3-indolyl)propanioic acid.

Example 4: Comparison Between K-12 *E. coli* and *S. aureus*

The data in Table 1 show that 5 of the 11 compounds tested exhibited various levels of antimicrobial activity against *E. coli* and *S. aureus*. These compounds, 2, 3, 5, 6, and 10 are more active against Gram-positive than Gram-negative bacteria. Indeed, the potency of 10 (MIC of 8 µM against K-12 *E. coli*) is twice that observed against *S. aureus* (4 µM). Most antibiotics are more potent against Gram-positive bacteria due to the absence of a secondary impermeable membrane (Nikaido, H., *Science* 1994, 264, 382-388). Of course, a Gram-positive specific target is also possible as observed for daptomycin (Straus and Hancock, *Biochem. Biophys. Acta* 2006, 1758, 1215-1223).

Example 5: Structural Comparison

The compounds studied fall into two categories: compounds having arenyl or alkyl spacers. The compounds that have aromatic spacers are 5 (ortho), 1-4 (meta), and 6 (para). The alkylene spacers range from three to twelve methylenes in 7-10. Compound 11 contains a single tryptophan (no spacer) and is intended to serve as a control.

The arylene BTs are more active antimicrobials than those having alkyl spacers except for 10 [$(CH_2)_{12}$ (L-Trp)], the most potent compound against the three strains of bacteria tested. Note that 11, the single Trp control, is essentially inactive (MIC>128 µM). Compounds 1 and 2 are identical except that the two amino acids are glycine in the former and tryptophan in the latter. Compound 2 showed modest antimicrobial activity and 1 showed none (MIC>128 µM) against all three bacteria. The activity of 2 was also lost when tryptophan was replaced by 3-(3-indolyl)propanoic acid (4). It was inferred that both the charged ammonium moieties and the indoles in the tryptophan residues were critical for the activity of 2, 3, 5, 6, and 10. The disposition of the side chains in otherwise identical compounds 2, 5, and 6 revealed that ortho and meta substitution produced similar toxicities to the three subject bacteria, but essentially no activity was observed for para-phenylene bis(tryptophan) 6.

A further comparison can be made between 2 and 3, which differ only in the stereochemistry of the tryptophan residues. Both compounds showed similar activity against *E. coli* K-12 (64 µM) and *S. aureus* (32 µM). Compound 3, in which the tryptophans have the uncommon D-configuration, was nearly twice as active (28±4 µM) as the naturally occurring isomer L-tryptophan analog (2, 48±8 µM) against *E. coli* Tet[R]. Note that the MIC values in this case were narrowed from the power interval so that a closer comparison could be made. It was speculated that although both 2 and 3 were similarly toxic to *E. coli* Tet[R], the D-tryptophans were metabolized less rapidly (Vig, et al., *Pharm. Res.* 2003, 20, 1381-1388) and duration rather than potency was reflected in the different MICs.

The alkylene derivatives that approximate the molecular spacing of the tryptophans also showed relatively low activity against all three bacteria. Thus, compounds 7 and 8 are inactive. Compound 9 has a slightly longer spacer chain but was essentially inactive to all three bacterial strains. It was marginally more active against *E. coli* Tet[R] than it was against the *E. coli* K-12 or *S. aureus*, but it was generally less active than 2 or 3 against all three bacteria. However, the greater antimicrobial activity of $(CH_2)_{12}$ (L-Trp) (10) compared to meta-Ph (L-Trp) (2) and meta-Ph (D-Trp) (3) could relate to overall separation of the ammonium or tryptophan residues. The separation of —$NH_3^+$ groups in 10, the most active BT, is ~21 Å (fully extended alkyl chain). In 2 and 3, the separation is only ~12 Å. Of course, the phenylene BTs are more rigid than the alkyl BTs and the conformation of 10 in particular is currently unknown.

Amphiphiles are known to enhance the permeability of bacterial boundary layers (Lambert and Hammond, *Biochem. Biophys. Res. Commun.* 1973, 54, 796-799; and Hancock, *Lancet* 1997, 349, 418-422). Amphiphiles are also known to form aggregates in aqueous solution. An effort to detect aggregates of 10 was made by using dynamic light scattering (DLS). Compound 10 was deemed to be the most amphiphilic (bola-amphiphilic) of the structures owing to the estimated maximal spacing of the amino groups (Fuhrhop, et al., *J. Am. Chem. Soc.* 1993, 115, 1600-1601). Solutions of 10.(HCl)$_2$ at concentrations between 10 µM and 1 mM were prepared and examined by dynamic light scattering methods. At the highest concentration, it appeared that some aggregates formed, but the counts were low and the results were considered inconclusive.

Example 6: Cytotoxicity to Mammalian Cells

It was initially hypothesized that antimicrobial activity resulted from membrane disruption. Membrane active compounds are often cytotoxic to mammalian cells (Shai, *Biopolymers* 2002, 66, 236-48; Shai, et al., *Curr. Protein Pept. Sci.* 2006, 7, 479-86). The survival of three mammalian epithelial cell lines was assayed for 2, 3, 5, and 10. Inactive 6, para-Ph (L-Trp) and 7, $(CH_2)_3$ (L-Trp) were included as controls. The cell lines studied were human embryonic kidney (HEK-293), human cervix epithelial (HeLa, ATCC Accession No. CCL-2), and *Cercopithecus aethiops* kidney (Cos-7, ATCC Accession No. CRL 1651). HeLa cells were acquired from ATCC. Cos-7 and HEK-293 cells were donated by colleagues. Cell lines were regularly maintained in growth media containing DMEM (ATCC), 10% fetal bovine serum (FBS, ATCC) and 1% penicillin-streptomycin solution (ATCC). Adherent HEK-293, HeLa and Cos-7 cells were trypsinized using 0.25% (w/v) trypsin-EDTA (Sigma-Aldrich), suspended in a fresh media and diluted to get a concentration of $3 \times 10^5$ cells/ml. Cells were seeded in a 96-well plate (100 μL/well) to get $3 \times 10^4$ cells/well. The plates were incubated for 24 hours at 5% $CO_2$ and 37° C. to reach a confluency of 80-90%.

In a sterile 1.5 mL micro-centrifuge tube, compounds 2, 3, 5, 6, 7 and 10 (0.5% DMSO) were mixed with assay media (DMEM+10% FBS) and serially diluted by 2-fold each to get 2[MIC], [MIC], ½[MIC] and ¼ [MIC] concentrations. A control containing 0.5% DMSO was also prepared. After 24 hours, the spent media in the 96-well plate containing HEK-293, HeLa and Cos-7 cells (90% confluency) was replaced with 100 μL media containing the compounds 2, 3, 5, 6, 7 and 10 at various concentrations. The cells were incubated at 37° C. and 5% $CO_2$ for 24 hours before performing XTT assay (Sigma-Aldrich). The XTT assay was performed according to the manufacturer's protocol. After 24 hours of treatment with compounds, the media was replaced with PBS and 25 μL XTT was added to each well. The XTT assay works by the reduction of tetrazolium compound by alive cells to the colored soluble formazan product. The absorbance of the product was measured at 450 nm (XTT) and 690 nm (background). Percent survival was calculated by comparing the average absorbance of cells treated with compounds 2, 3, 5, 6, 7, and 10 to that of cells alone. Two replicates for each treatment were determined. Average percent survival and standard deviation were calculated.

Figure 2:
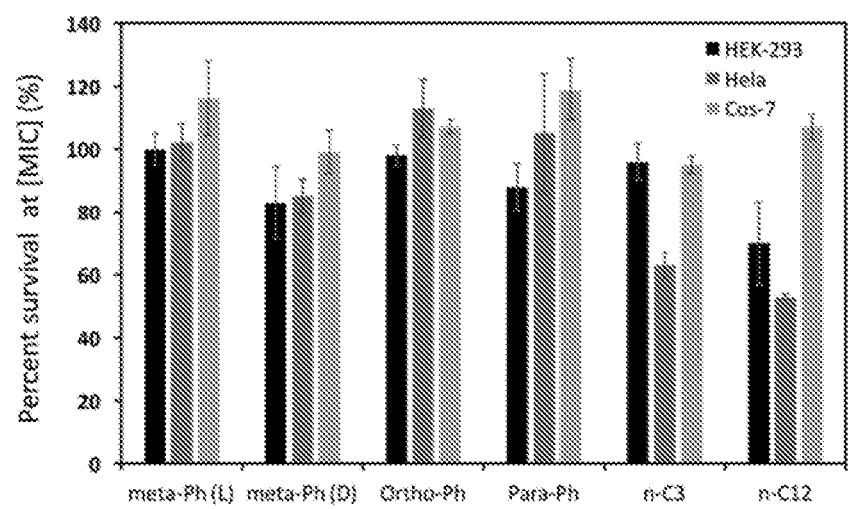
FIG. 2 illustrates cytotoxicity at the MIC concentration (against Tet$^R$ *E. coli*) of meta-Ph (L-Trp) (2, 48 µM), meta-Ph (D-Trp) (3, 28 µM), ortho-Ph (L-Trp) (5, 56 µM), para-Ph (L-Trp) (6, 120 µM), $(CH_2)_3$ (L-Trp) (7, 128 µM), and $(CH_2)_{12}$ (L-Trp) (10, 10 µM) to HEK-293, HeLa and Cos-7 cells. Error bars represents the standard deviation.

Cells were cultured for 24 h in 96-well plates and treated with media containing concentrations using [MIC] and [MIC]×2 determined previously for $Tet^R$ *E. coli*. The number of surviving cells was determined using an XTT assay (Sigma-Aldrich); the results are represented as percent survival in FIG. 2. Cells alone were used as controls and established 100% survival. The data represent two replicates of three trials and the error bars represent the standard deviation.

At MIC concentrations, arene-linked BTs 2, 3, 5, and 6 showed 100% survival against HEK-293, HeLa, or Cos-7 cells. Alkyl-linked 7 and 10 were minimally toxic to HEK-293 or Cos-7 cells, but were moderately toxic to HeLa cells. In general, the survival of Cos-7 cells was unaffected by the highest concentrations of all the compounds tested.

Figure 3:
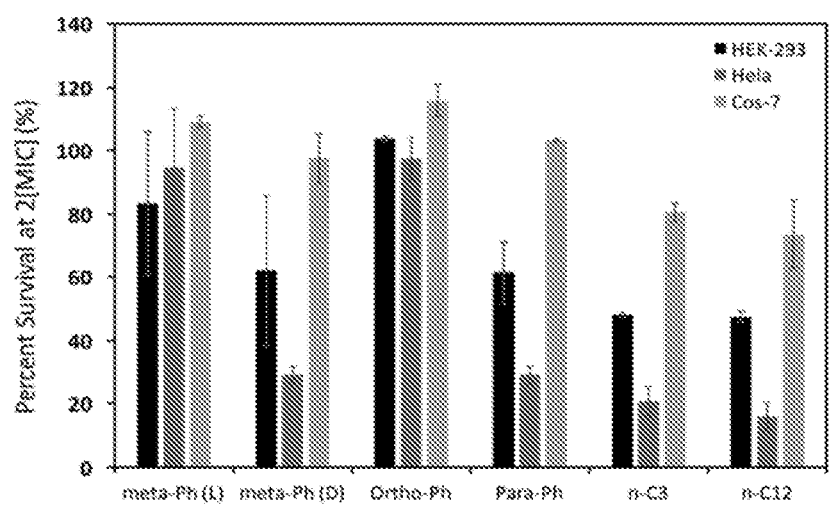
FIG. 3 illustrates the cytotoxicity at twice the MIC concentration (against Tet$^R$ *E. coli*) of meta-Ph (L-Trp) (2, 96 µM), meta-Ph (D-Trp) (3, 56 µM), ortho-Ph (L-Trp) (5, 112 µM), para-Ph (L-Trp) (6, 240 µM), $(CH_2)_3$ (L-Trp) (7, 256 µM) and $(CH_2)_{12}$ (L-Trp) (10, 20 µM) to HEK-293, HeLa and Cos-7 cells. Error bars represent the standard deviation.

The survival of all three cell lines was unaffected by a two-fold increase in concentration of meta-Ph (L-Trp) (2, 56 μM) and ortho-Ph (L-Trp) (5, 112 μM), (FIG. 3). In contrast, meta-Ph (D-Trp) (3) at (96 μM) showed 62% survival for HEK-293 and 29% for HeLa cells. The para-Ph (L-Trp) (6) at 240 μM, showed 61% survival for HEK-293 and 29% for HeLa cells. It is noted that the cytotoxicities for D-tryptophan (3) and para-Ph L-tryptophan (6) were observed at high concentrations: 96 μM and 240 μM respectively.

Two observations can be made from the data in FIG. 3 concerning alkyl BTs 7 and 10. First, 7 and 10 were more cytotoxic than phenylene BTs 2, 3, 5, or 6. At the MIC concentrations of $(CH_2)_3$ (L-Trp) (7, 128 μM) and $(CH_2)_{12}$ (L-Trp) (10, 10 μM), 80-100% survival was observed against HEK-293 and Cos-7 cells (see, FIG. 2). At twice the MIC concentrations of 7 (256 μM) and 10 (20 μM), survival for HEK-293 and Cos-7 further decreased to 50-80% (see, FIG. 3). It was inferred that alkyl-linked BTs may find use as antimicrobials.

Second, the cytotoxicity of $(CH_2)_3$ (L-Trp) (7) and $(CH_2)_{12}$ (L-Trp) (10) was greater against HeLa cells than either HEK-293 or Cos-7 cell lines. The HeLa cells are adenocarcinoma involved cervical epithelial cells. The selectivity of $(CH_2)_{12}$ (L-Trp) (10) at 20 μM for HeLa cells over HEK-293 and Cos-7 suggests a potential application in cancer chemotherapy. It is noted that a $(CH_2)_8$ (L-Trp) analog of 10 prepared by Lown and co-workers showed promising cytotoxicity against 60 human cancer cell lines (Kumar, et al., *Oncol. Res.* 2003, 14, 247-265).

Example 7: Recovery of Antimicrobial Activity Against a Resistant Strain

The cytotoxicity of the compounds 2, 3, 5, 6, 7 and 10 was minimal at MIC concentrations. Next, it was determined whether these compounds could be used at concentrations of ½ MIC or lower to recover the activity of antibiotics against efflux pump expressing resistant bacteria. At these lower concentrations there should be no cytotoxicity. In addition, at the half-MIC concentrations, these compounds should not have any effect on bacterial growth. It was hypothesized that if certain BTs increased membrane permeability, they could recover antimicrobial potency against efflux-based resistance. This hypothesis was tested with the $Tet^R$ strain of *E. coli*.

First, MICs were determined for compounds 2, 3, 5, 6, 7, and 10 against $Tet^R$ *E. coli*. Compounds 6 (para-Ph) and 7 (n-$C_3$) were also included as controls. The MICs against $Tet^R$ *E. coli* were refined compared to the power series and are reported as a range in Table 1 above. The MICs of tetracycline and ampicillin against $Tet^R$ *E. coli* were 900±100 μM and >1000 μM, respectively. For comparison, the MIC for tetracycline against non-resistant *E. coli* K-12 is ~3 μM. Ampicillin was used to maintain selective pressure for the expression of pBR322 plasmid. Ampicillin was omitted from experiments that contained tetracycline. Next, the MIC of tetracycline was determined when co-administered with 2, 3, 5, 6, 7, or 10. The results are recorded in Table 2. The results are represented as the MIC of tetracycline in the presence of the indicated BTs. The fold-recovery was determined by dividing the MIC of tetracycline when used alone by the MIC of tetracycline determined in the presence of the compounds.

TABLE 2

Recovery of tetracycline activity against $Tet^R$ *E. coli*

| Compounds Used | [Compound] μM | MIC [Tet] μM[a] | Fold Recovery | FIC[c] |
| --- | --- | --- | --- | --- |
| None | 0 | 900 | n.a.[b] | n.a. |
| meta-Ph (L-Trp) (2) | 24 [½ MIC] | 56.25 | 16-fold | 0.56 |
| meta-Ph (L-Trp) (2) | 12 [¼ MIC] | 112.5 | 8-fold | 0.38 |
| meta-Ph (L-Trp) (2) | 14 | 112.5 | 8-fold | 0.42 |
| meta-Ph (D-Trp) (3) | 14 [½ MIC] | 112.5 | 8-fold | 0.63 |

TABLE 2-continued

Recovery of tetracycline activity against Tet$^R$ E. coli

| Compounds Used | [Compound] μM | MIC [Tet] μM$^a$ | Fold Recovery | FIC$^c$ |
|---|---|---|---|---|
| metao-Ph (D-Trp) (3) | 7 [¼ MIC] | 225 | 4-fold | 0.50 |
| ortho-Ph (L-Trp) (5) | 28 [½ MIC] | 112.5 | 8-fold | 0.63 |
| ortho-Ph (L-Trp) (5) | 14 [¼ MIC] | 225 | 4-fold | 0.50 |
| para-Ph (L-Trp) (6) | 60 [½ MIC] | 112.5 | 8-fold | 0.63 |
| para-Ph (L-Trp) (6) | 30 [¼ MIC] | 225 | 4-fold | 0.50 |
| para-Ph (L-Trp) (6) | 14 | 450 | 2-fold | 0.62 |
| n-C$_3$ (L-Trp) (7) | 60 [½ MIC] | 112.5 | 8-fold | 0.63 |
| n-C$_3$ (L-Trp) (7) | 30 [¼ MIC] | 112.5 | 8-fold | 0.38 |
| n-C$_3$ (L-Trp) (7) | 5 | 450 | 2-fold | 0.54 |
| n-C$_{12}$ (L-Trp) (10) | 5 [½ MIC] | 225 | 4-fold | 0.75 |
| n-C$_{12}$ (L-Trp) (10) | 2.5 [¼ MIC] | 450 | 2-fold | 0.75 |

$^a$MIC is the observed inhibitory concentration of tetracycline in the presence of the indicated compound. MIC values represent two trials of two replicates each. MIC resolution is in powers of 2.
$^b$'n.a.' means not applicable.
$^c$FIC is the fractional inhibitory concentration Tetracycline activity was recovered by compounds 2, 3, 5, 6, 7 and 10 at ½ and ¼ of its MIC values. This recovery of tetracycline potency was based on the concentration and the structure of the compounds used. The highest recovery of tetracycline activity was observed with meta-Ph (L-Trp) (2). The MIC of tetracycline was decreased from 900 μM to 56.25 μM in the presence of 24 μM of compound 2. At twice the concentration of compound 2 (48 μM), no cytotoxicity to HEK-293, HeLa, and Cos-7 cells was apparent (see, FIG. 2). The (CH$_2$)$_{12}$ (L-Trp) (10), most potent antimicrobial in the 1-10 group, showed 2 to 4-fold recovery of tetracycline activity.

The fractional inhibitory concentration (FIC) is often used as a measure of synergism or antagonism in comparing two or more compounds (Berenbaum, Pharmacol. Rev. 1989, 41, 93-141). The FIC is the sum of the fraction of the MIC for each compound used. Synergy is defined broadly as FIC<1, or more conservatively as FIC≤0.5. Under the broad definition, all compounds tested can be said to have at least moderate synergy with tetracycline. All arene-based compounds fit the more conservative definition of synergy with FIC values of 0.5 or less at the tested concentrations. Compound 2 showed particularly high synergy with a FIC of 0.38. The shorter alkyl-linked compound 7 also had a FIC of 0.38, whereas the longer n-C$_{12}$ (L-Trp) (10) did not show synergy below a FIC of 0.75.

Figure 4:
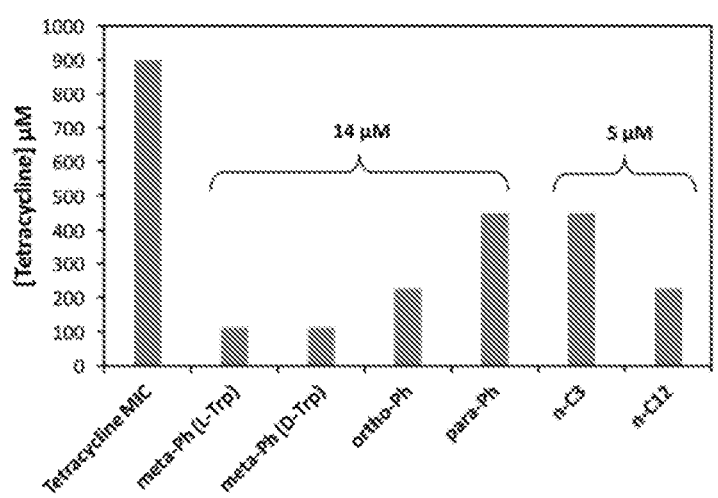
FIG. 4 illustrates the comparison of the ability of meta-ph (L-Trp) (2, 14 µM), meta-ph (D-Trp) (3, 14 µM), ortho-ph (L-Trp) (5, 14 µM), para-ph (L-Trp) (6, 14 µM), $(CH_2)_3$ (L-Trp) (7, 5 µM) and $(CH_2)_{12}$ (L-Trp) (10, 5 µM) to recover tetracycline activity against Tet$^R$ *E. coli*. MICs were reproduced three times and the resolution is in powers of 2.

Since the MICS of all the compounds tested were different, a single concentration was chosen to compare the efficacies of different compounds in the expectation that if any trend was apparent, it would be revealed. The ability of compounds 2, 3, 5 and 6 was compared to recover tetracycline activity at 14 μM, which is much lower than the MIC observed with any arene-spacer based compounds. The alkyl-spacer based compounds (3 and 12) were compared at 5 μM, which is much lower than the MIC observed with either compound. It is apparent from the graph of FIG. 4 that at 14 μM meta-Ph (L-Trp), 2, is most effective at recovering tetracycline activity against Tet$^R$ E. coli. The least effective synergists were those having para-Ph, 6, or propylene (n-C$_3$), 7, spacers. Clearly, regiochemistry and conformational mobility are contributors to the observed differences but the precise nature of the influence(s) is not known.

Example 8: Antimicrobial Activity Against *Staphylcoccus aureus* 1199B

Figure 5A:
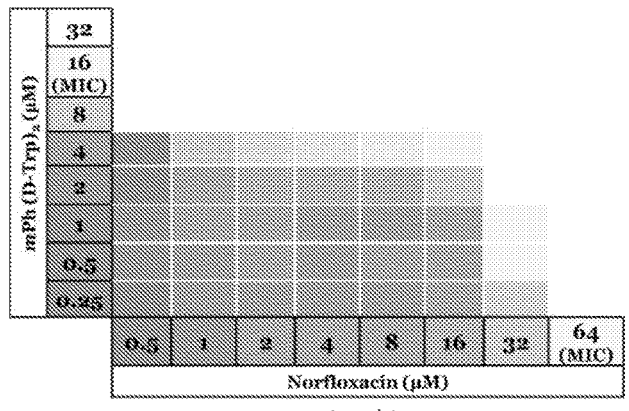
FIG. 5A/B/C illustrate various compounds' antimicrobial activities against *Staphylcoccus aureus* 1199B in the "checkerboard" format.
Figure 5A:
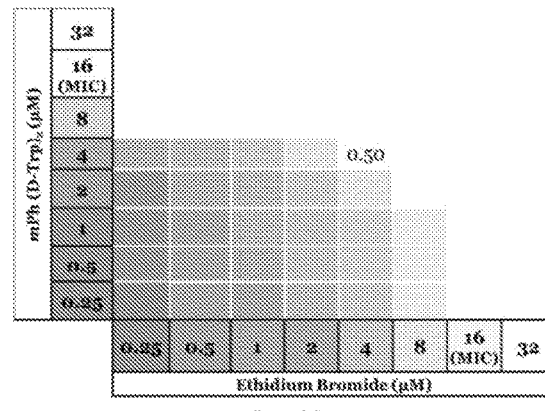
Figure 5B:
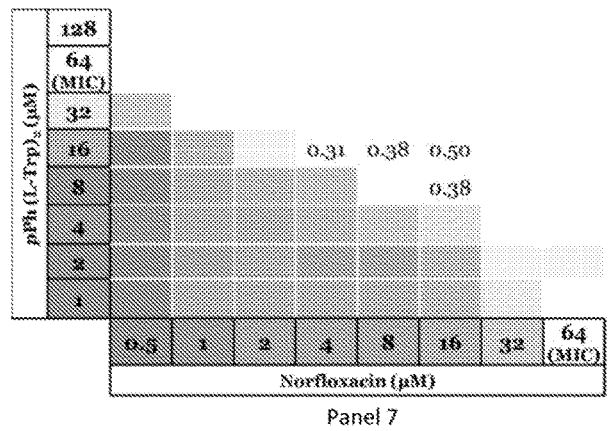
Figure 5B:
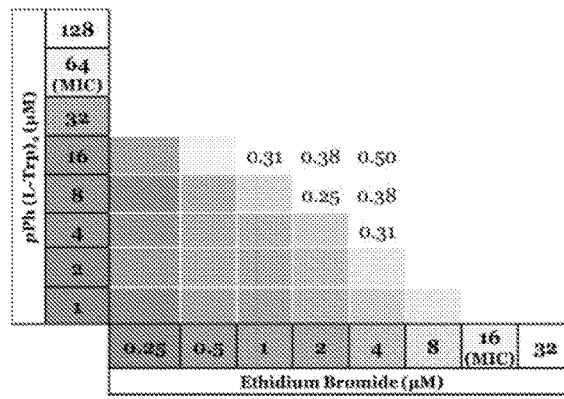
Figure 5B:
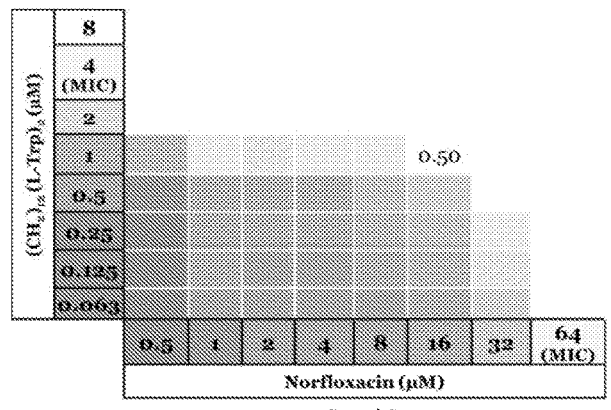
Figure 5B:
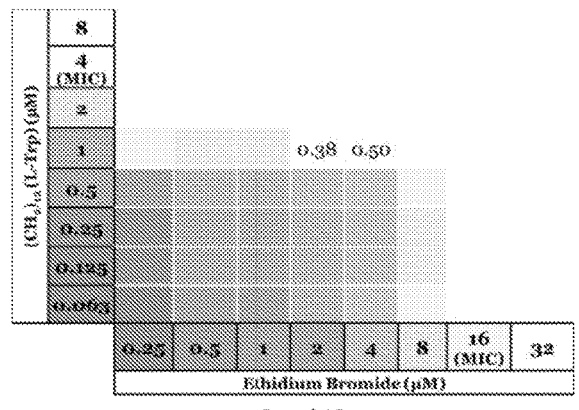
Figure 5B:
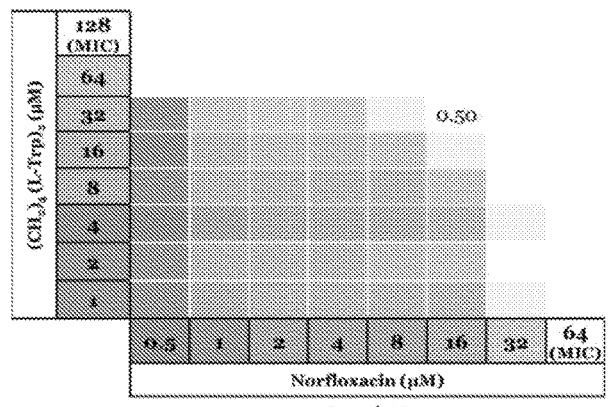
Figure 5B:
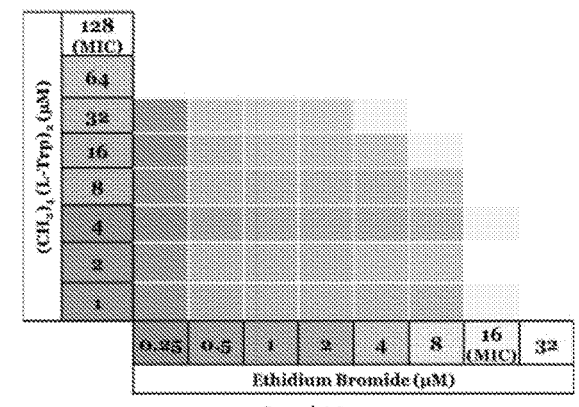
Figure 5C:
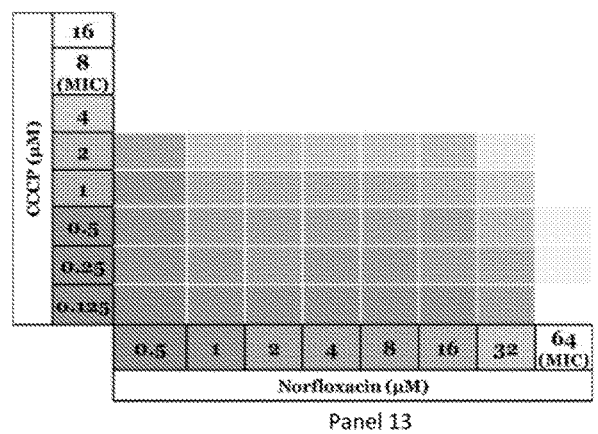
Figure 5C:
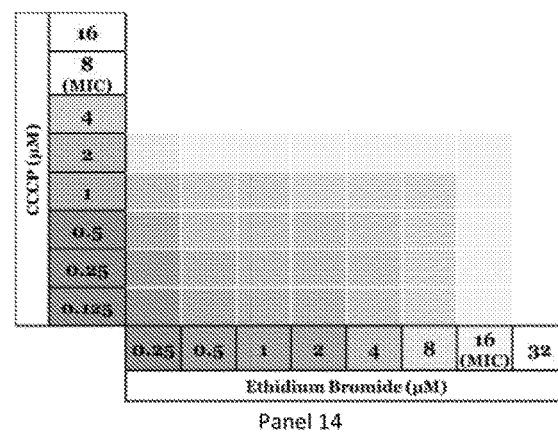

Similar experiments to those described in Example 7 above were conducted, wherein the antimicrobial activity of various compounds was determined against *Staphylcoccus aureus* 1199B. The results are shown in the "checkerboard" format (see, fourteen panels illustrated in FIG. 5A/B/C). The bacterial strain *Staphylcoccus aureus* 1199B contains the Nor A efflux pump which causes resistance to both norfloxacin and ethidium bromide. The compounds under study are listed in the left column and the additives are listed in the right column of Table 3 below. Norfloxacin is an FDA approved commercial antibiotic. Ethidium bromide is a DNA-binding dye that also shows antibiotic properties. CCCP is a known efflux pump inhibitor and served as a control.

The results show that synergistic activity was observed in panel numbers 2, 3, 4, 6, 7, 8, 9, 10, and 11. In the presence of ½ MIC or 2 μM of, L-Typ-C$_{12}$-Ph-L-Trp, activity was recovered by 128-fold.

TABLE 3

Compounds and Additives

| Panel | Compound | Additive |
|---|---|---|
| 1 | D-Typ-meta-Ph-D-Trp | Norfloxacin |
| 2 | D-Typ-meta-Ph-D-Trp | Ethidium bromide |
| 3 | L-Typ-meta-Ph-L-Trp | Norfloxacin |
| 4 | L-Typ-meta-Ph-L-Trp | Ethidium bromide |
| 5 | L-Typ-ortho-Ph-L-Trp | Norfloxacin |
| 6 | L-Typ-ortho-Ph-L-Trp | Ethidium bromide |
| 7 | L-Typ-para-Ph-L-Trp | Norfloxacin |
| 8 | L-Typ-para-Ph-L-Trp | Ethidium bromide |
| 9 | L-Typ-C$_{12}$-Ph-L-Trp | Norfloxacin |
| 10 | L-Typ-C$_{12}$-Ph-L-Trp | Ethidium bromide |
| 11 | L-Typ-C$_4$-Ph-L-Trp | Norfloxacin |
| 12 | L-Typ-C$_4$-Ph-L-Trp | Ethidium bromide |
| 13 | Carbonyl cyanide m-chlorophenyl hydrazine (CCCP) | Norfloxacin |
| 14 | Carbonyl cyanide m-chlorophenyl hydrazine (CCCP) | Ethidium bromide |

Example 9: Membrane Permeability

To test the membrane permeability of the Tet$^R$ E. coli, the bacteria was first grown overnight from one CFU in media containing 100 μg/mL Ampicillin at 37° C. and 200 RPM. Tet$^R$ E. coli was then knocked back to O.D. 600 nm=0.550 before use. In a sterile test tube, cells were added followed by either compounds 2 or 10 at half-MIC concentrations and incubated at 37° C. and 200 RPM. The concentration of DMSO was kept constant at 0.5% —by volume in each case. After 30 minutes of incubation, the cells were washed by centrifugation at 3000×g for 5 minutes and re-suspended in sterile phosphate buffered saline (PBS). Propidium iodide (30 μM, Thermo-Fischer) and fluorescein diacetate (60 μM, Sigma-Aldrich) were added to the Tet$^R$ E. coli cells in the PBS, mixed by vortexing and incubated at 37° C. and 200 RPM. After 30 minutes, the cells were washed again by centrifugation at 3000×g for 5 minutes. The pellet was suspended in a fresh PBS, loaded onto a clean glass slide, covered with a cover slip and observed under Zeiss LSM 700 confocal microscope.

To test the permeability of HEK-293 cells, the cells were cultured in growth medium as described above. HEK-293 (90% confluent) were then seeded in a 96-well plate to get 30,000 cells/well. After 24 hours of incubation at 37° C. and 5% CO$_2$, the spent media was replaced with media (DMEM and 10% FBS) containing compound 2 at either 20 μM or 80 μM. The 80 μM concentration was used to confirm the cytotoxicity of the compound 2 and to make sure that serum did not inhibit its activity. Triton X-100 at 0.1%—by volume (1670 μM) and DMSO 0.5% (v/v) were also used as controls. After 2 hours of incubation, spent media was replaced with PBS containing propidium iodide (30 μM) and fluorescein diacetate (60 μM) and incubated at 37° C. and 5% $CO_2$. After 2 hour of incubation, the spend media was replaced with fresh PBS and the cells were observed under Zeiss LSM 700 confocal microscope. The images were reported without any alterations. The gain and the intensity in all the images were kept constant.

Based on the MIC and toxicity studies, meta-Ph (L-Trp), 2, and $(CH_2)_{12}$ (L-Trp), 10, have emerged as compounds of interest for different reasons. The meta-Ph (L-Trp), 2, showed synergy against tetracycline resistant *E. coli*, without any cytotoxicity to three mammalian cell lines. Dodecylene BT, 10, showed the greatest antimicrobial activity, but also exhibited cytotoxicity to HEK-293 and HeLa cells. In order for the BTs to exhibit toxicity to any of the microbes, it is essential for them to penetrate the bacterial membrane. In Gram-negative organisms, the boundary membrane consists of two layers although porins are present within them that could pass these relatively small molecules.

Figure 6:
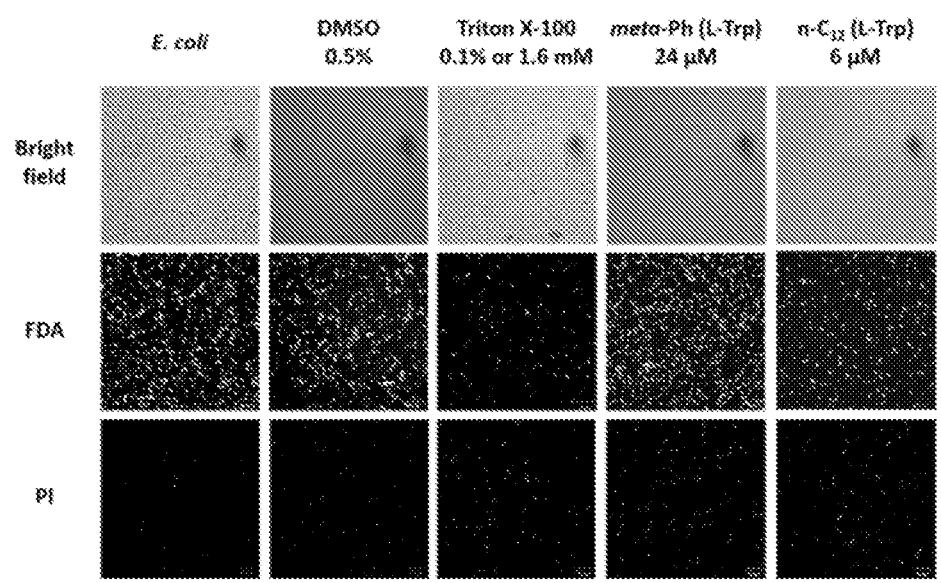
FIG. 6 illustrates Tet$^R$ E. coli cell membrane permeability by compounds 2 (meta-Ph (L-Trp)) and 10 ($C_{12}$-Trp) at ~½ MIC and controls.

FIG. 6 shows the results of a confocal microscopy study using *E. coli* $Tet^R$ as the test organism. The study was designed to assess the membrane permeability and viability of the *E. coli* in the presence of BTs 2 and 10. The three panels in FIG. 6 show the bright field (BF) microscopic images (top row), the result when fluorescein diacetate (FDA) is present (middle row), and the presence of propidium iodide (PI, bottom row), if any. Propidium iodide does not normally pass through boundary membranes into bacteria or other cells. When it does, it intercalates in DNA, which leads to enhanced fluorescence. Fluorescein diacetate is incorporated into the cells during growth, but is not fluorescent. If the organism is or remains vital, the diester will be hydrolyzed and fluorescein will be observed by its fluorescence emission.

The membrane permeability and viability of *E. coli* $Tet^R$ was observed for the microbe alone or in the presence of BTs 2 or 10. Controls for the permeability/viability assay were included for *E. coli* in the presence of a final concentration of 0.5% (v/v) DMSO (the vehicle for administration of BTs), and a final concentration of 0.1% (w/w) Triton X-100. It was recently demonstrated that while small amounts of DMSO (e.g. 0.5% in media) did not alter biological activity, at higher concentrations and with certain organisms there was an effect (Negin, et al., *RSC Adv.* 2015, 5, 8088-8093). Thus, less than or equal to 0.5% DMSO (v/v) was always used; the control is shown in the second column. Triton X-100 is a potent detergent, which was used at 0.1% or ~1,670 μM.

The images show that *E. coli* $Tet^R$ alone or in the presence of 0.5% DMSO were vital. This was also the case when *E. coli* $Tet^R$ was subjected to 2 at 24 μM or 10 at 6 μM. These concentrations were selected because each is ½ the MIC value. The lower row of FIG. 6 shows that propidium iodide does not infiltrate *E. coli* $Tet^R$ in the absence of Triton X-100, 2, or 10. When Triton X-100 was the adjuvant, essentially all the cells were killed and the presence of PI may simply be part of the cellular detritus. Propidium iodide fluorescence was observed when 2 or 10 was added to the cells. This indicates that the membrane permeability has increased, yet cells remain vital at the concentrations tested (cf. FDA fluorescence).

Figure 7:
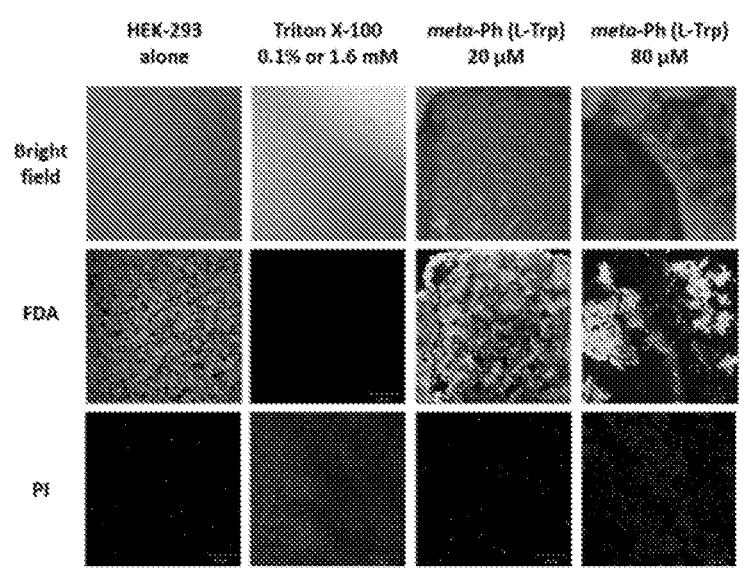
FIG. 7 illustrates mammalian cell permeability in HEK-293 in the presence of meta-Ph (L-Trp), 2, at 20 μM and 80 μM.

A compound that inhibits bacterial growth and penetrates into the microbe's cytosol may also penetrate into mammalian cells. A similar microscopic study was conducted with the human embryonic kidney (HEK-293) cell line. In this case, only compound 2 was studied. Its activity (MIC) against all three microbes ranged from 32-64 μM. The microscopic study was therefore conducted at 20 μM, a value well below any inhibitory concentration, and at 80 μM, a concentration above all three MIC values. The 80 μM concentration was used to confirm the cytotoxicity of 2 and to establish the lack of serum inhibition. The results are shown in FIG. 7.

Propidium iodide indicates an increase of the membrane permeability of HEK-293 cells and the FDA fluorescence and reports cellular vitality. When Triton X-100 was administered at 0.1% (~1670 μM), vitality was lost and a strong signal from propidium iodide reflected interaction of the dye with dispersed DNA. The results for 2 at 20 μM and 80 μM show that at the lower concentration, a relatively low level of PI penetration was apparent and there was no loss of vitality. At 80 μM, there was considerable penetration of PI and some toxic effect was apparent.

These data indicate that at sub-lethal concentrations, meta-Ph (L-Trp), 2, increases the membrane permeability of *E. coli* cells, but shows no cytotoxicity or permeability alteration for HEK-293 mammalian cells. At higher concentrations, both cytotoxicity and membrane disruption are manifested.

Having illustrated and described the principles of the present invention, it should be apparent to persons skilled in the art that the invention can be modified in arrangement and detail without departing from such principles. Those skilled in the art will recognize, or be able to ascertain using no more than routine experimentation, many equivalents to the specific embodiments of the invention described herein. Such equivalents are intended to be encompassed by the following claims.

All publications and published patent documents cited in this specification are incorporated herein by reference to the same extent as if each individual publication or patent application was specifically and individually indicated to be incorporated by reference.

What claimed is:

1. An antimicrobial composition comprising a bis(tryptophan) derivative, wherein said bis(tryptophan) derivative comprises: (i) an arenyl, an alkyl, an aralkyl, or an unsaturated spacer; (ii) a charged ammonium moiety; and (iii) an indole in a tryptophan residue.

2. The antimicrobial composition of claim 1, wherein said bis(tryptophan) derivative is selected from the group consisting of (2S,2'S)-1,1'-(1,3-phenylenebis(azanediyl))bis(3-(1H-indol-3-yl)-1-oxopropan-2-aminium) chloride, (2R,2'R)-1,1'-(1,3-phenylenebis(azanediyl))bis(3-(1H-indol-3-yl)-1-oxopropan-2-aminium) chloride, (2S,2'S)-1,1'-(1,2-phenylenebis(azanediyl))bis(3-(1H-indol-3-yl)-1-oxopropan-2-aminium) chloride, (2S,2'S)-1,1'-(1,4-phenylenebis(azanediyl))bis(3-(1H-indol-3-yl)-1-oxopropan-2-aminium) chloride, and (S)-1-((12-((R)-2-ammonio-3-(1H-indol-3-yl)propanamido)dodecyl)amino)-3-(1H-indol-3-yl)-1-oxopropan-2-aminium chloride.

3. A method of recovering or enhancing antimicrobial activity of an antibiotic wherein said method comprising administering to a microbe the antibiotic with the antimicrobial composition comprising a bis(tryptophan) derivative of claim 1, and wherein said microbe is a bacterium.

4. The method of claim 3, wherein said bis(tryptophan) derivative is selected from the group consisting of (2S,2'S)-1,1'-(1,3-phenylenebis(azanediyl))bis(3-(1H-indol-3-yl)-1-oxopropan-2-aminium) chloride, (2R,2'R)-1,1'-(1,3-phenylenebis(azanediyl))bis(3-(1H-indol-3-yl)-1-oxopropan-2-aminium) chloride, (2S,2'S)-1,1'-(1,2-phenylenebis (azanediyl))bis(3-(1H-indol-3-yl)-1-oxopropan-2-aminium) chloride, (2S,2'S)-1,1'-(1,4-phenylenebis(azanediyl))bis(3-(1H-indol-3-yl)-1-oxopropan-2-aminium) chloride, and (S)-1-((12-((R)-2-ammonio-3-(1H-indol-3-yl)propanamido)dodecyl)amino)-3-(1H-indol-3-yl)-1-oxopropan-2-aminium chloride.

5. The method of claim 3, wherein said bacterium is an efflux pump expressing Gram-positive or Gram-negative bacterium, and said antibiotic resistance is efflux pump-mediated resistance.

6. The method of claim 5, wherein said bacterium is an *Escherichia coli* strain or a *Staphylococcus aureus* strain.

7. The method of claim 3, wherein said antibiotic is administered at a concentration below its minimum inhibitory concentration.

8. The method of claim 3, wherein said bis(tryptophan) derivative is administered at a concentration below its minimum inhibitory concentration.

9. The method of claim 3, wherein said antibiotic and said bis(tryptophan) derivative are both administered at a concentration below their minimum inhibitory concentrations.

10. The method of claim 3, wherein said antibiotic is selected from the group consisting of ampicillin, kanamycin, tobramycin, erythromycin, rifampicin, norfloxacin, and tetracycline.

11. The method of claim 10, wherein said antibiotic is ampicillin, norfloxacin or tetracycline.

\* \* \* \* \*